(12) United States Patent
Dorian et al.

(10) Patent No.: US 8,337,711 B2
(45) Date of Patent: Dec. 25, 2012

(54) SYSTEM AND PROCESS FOR SEPARATING A MATERIAL

(75) Inventors: Randel Dorian, San Diego, CA (US); Michael D. Leach, Warsaw, IN (US); Richard W. Storrs, Berkeley, CA (US); Jason Chavarria, Warsaw, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 872 days.

(21) Appl. No.: 12/395,085

(22) Filed: Feb. 27, 2009

(65) Prior Publication Data

US 2009/0221075 A1    Sep. 3, 2009

Related U.S. Application Data

(60) Provisional application No. 61/032,619, filed on Feb. 29, 2008, provisional application No. 61/078,178, filed on Jul. 3, 2008.

(51) Int. Cl.
*B01D 21/26* (2006.01)
*B04B 3/00* (2006.01)

(52) U.S. Cl. ............ 210/782; 210/789; 210/360.1; 210/380.1; 210/516; 422/72; 422/527; 604/6.01; 604/6.15; 604/403

(58) Field of Classification Search ............ 210/782, 210/789, 360.1, 380.1, 516; 422/72, 527; 604/6.01, 6.15, 403
See application file for complete search history.

(56) References Cited

U.S. PATENT DOCUMENTS

| | | |
|---|---|---|
| 280,820 A | 7/1883 | Hickson et al. |
| 593,333 A | 11/1897 | Park |
| 1,468,313 A | 9/1923 | Lux |
| 1,593,814 A | 7/1926 | Vogel |
| 2,722,257 A | 11/1955 | Lockhart |
| 3,013,557 A | 12/1961 | Pallotta |
| 3,141,846 A | 7/1964 | Laven, Jr. |
| 3,159,159 A | 12/1964 | Cohen |
| 3,409,165 A | 11/1968 | Creith |
| 3,420,374 A | 1/1969 | Umeda |
| 3,441,143 A | 4/1969 | Kudlaty |
| 3,453,364 A | 7/1969 | Flodin et al. |
| 3,469,369 A | 9/1969 | Helmke |
| 3,508,653 A | 4/1970 | Coleman |
| 3,545,671 A | 12/1970 | Ross |
| 3,583,627 A | 6/1971 | Wilson |

(Continued)

FOREIGN PATENT DOCUMENTS
AU    696278    1/1999
(Continued)

OTHER PUBLICATIONS

International Preliminary Examination Report and Written Opinion issued Aug. 31, 2010 for PCT/US2009/035564 claiming benefit of U.S. Appl. No. 61/078,178, filed Jul. 3, 2008 of which U.S. Appl. No. 12/395,085, filed Feb. 27, 2009 claims benefit.

(Continued)

*Primary Examiner* — David A Reifsnyder
(74) *Attorney, Agent, or Firm* — Harness, Dickey

(57) ABSTRACT

Disclosed is a system to separate, enrich, and/or purify a cellular population from a biological tissue, such as a tissue sample. For example, an adipose tissue sample can be acquired and disrupted. The disrupted tissue sample can then be separated and purified. The separated components can include multipotent, pluripotent, or other cell populations.

39 Claims, 18 Drawing Sheets

U.S. PATENT DOCUMENTS

| | | |
|---|---|---|
| 3,593,915 A | 7/1971 | Steinacker |
| 3,596,652 A | 8/1971 | Winkelman |
| 3,647,070 A | 3/1972 | Adler |
| 3,654,925 A | 4/1972 | Holderith |
| 3,661,265 A | 5/1972 | Greenspan |
| 3,706,305 A | 12/1972 | Berger et al. |
| 3,706,306 A | 12/1972 | Berger et al. |
| 3,723,244 A | 3/1973 | Breillatt, Jr. |
| 3,741,400 A | 6/1973 | Dick |
| 3,779,383 A | 12/1973 | Ayres |
| 3,785,549 A | 1/1974 | Latham, Jr. |
| 3,814,248 A | 6/1974 | Lawhead |
| 3,849,072 A | 11/1974 | Ayres |
| 3,850,369 A | 11/1974 | Bull et al. |
| 3,879,295 A | 4/1975 | Glover et al. |
| 3,887,466 A | 6/1975 | Ayres |
| 3,894,952 A | 7/1975 | Ayres |
| 3,896,733 A | 7/1975 | Rosenberg |
| 3,897,337 A | 7/1975 | Ayres |
| 3,897,343 A | 7/1975 | Ayres |
| 3,909,419 A | 9/1975 | Ayres |
| 3,929,646 A | 12/1975 | Adler |
| 3,931,010 A | 1/1976 | Ayres et al. |
| 3,931,018 A | 1/1976 | North, Jr. |
| 3,935,113 A | 1/1976 | Ayres |
| 3,937,211 A | 2/1976 | Merten |
| 3,941,699 A | 3/1976 | Ayres |
| 3,945,928 A | 3/1976 | Ayres |
| 3,951,801 A | 4/1976 | Ayres |
| 3,957,654 A | 5/1976 | Ayres |
| 3,962,085 A | 6/1976 | Liston et al. |
| 3,965,889 A | 6/1976 | Sachs |
| 3,972,812 A | 8/1976 | Gresl, Jr. |
| 3,982,691 A | 9/1976 | Schlutz |
| 4,001,122 A | 1/1977 | Griffin |
| 4,020,831 A | 5/1977 | Adler |
| 4,046,699 A | 9/1977 | Zine, Jr. |
| 4,055,501 A | 10/1977 | Cornell |
| 4,059,108 A | 11/1977 | Latham, Jr. |
| 4,066,549 A | 1/1978 | Oeser et al. |
| 4,077,396 A | 3/1978 | Wardlaw et al. |
| 4,088,582 A | 5/1978 | Murty et al. |
| 4,146,172 A | 3/1979 | Cullis et al. |
| 4,152,270 A | 5/1979 | Cornell |
| 4,154,690 A | 5/1979 | Ballies et al. |
| 4,159,896 A | 7/1979 | Levine et al. |
| 4,187,979 A | 2/1980 | Cullis et al. |
| 4,189,385 A | 2/1980 | Greenspan |
| 4,203,840 A | 5/1980 | Stoeppler et al. |
| 4,204,537 A | 5/1980 | Latham, Jr. |
| 4,225,580 A | 9/1980 | Rothman et al. |
| 4,229,298 A | 10/1980 | Bange |
| 4,269,718 A | 5/1981 | Persidsky |
| 4,294,707 A | 10/1981 | Ikeda et al. |
| 4,298,598 A | 11/1981 | Schwarz et al. |
| 4,300,717 A | 11/1981 | Latham, Jr. |
| 4,303,193 A | 12/1981 | Latham, Jr. |
| 4,314,823 A | 2/1982 | Rich, Jr. et al. |
| 4,322,298 A | 3/1982 | Persidsky |
| 4,332,351 A | 6/1982 | Kellogg et al. |
| 4,362,567 A | 12/1982 | Schwarz et al. |
| 4,364,832 A | 12/1982 | Ballies |
| 4,377,572 A | 3/1983 | Schwarz et al. |
| 4,379,849 A | 4/1983 | Heimreid |
| 4,411,794 A | 10/1983 | Schwinn et al. |
| 4,414,976 A | 11/1983 | Schwarz et al. |
| 4,416,654 A | 11/1983 | Schoendorfer et al. |
| 4,417,981 A | 11/1983 | Nugent |
| 4,424,132 A | 1/1984 | Iriguchi et al. |
| 4,427,650 A | 1/1984 | Stroetmann et al. |
| 4,427,651 A | 1/1984 | Stroetmann et al. |
| 4,442,655 A | 4/1984 | Stroetmann et al. |
| 4,443,345 A | 4/1984 | Wells |
| 4,446,021 A | 5/1984 | Aufderhaar et al. |
| 4,453,927 A | 6/1984 | Sinko |
| 4,453,939 A | 6/1984 | Zimmerman et al. |
| 4,464,167 A | 8/1984 | Schoendorfer et al. |
| 4,511,662 A | 4/1985 | Baran et al. |
| 4,537,767 A | 8/1985 | Rothman et al. |
| RE32,089 E | 3/1986 | Blatt et al. |
| 4,577,514 A | 3/1986 | Bradley et al. |
| 4,610,656 A | 9/1986 | Mortensen |
| 4,617,009 A | 10/1986 | Ohlin et al. |
| 4,627,879 A | 12/1986 | Rose et al. |
| 4,631,055 A | 12/1986 | Redl et al. |
| 4,632,761 A | 12/1986 | Bowers et al. |
| 4,639,316 A | 1/1987 | Eldegheidy |
| 4,650,678 A | 3/1987 | Fuhge et al. |
| 4,655,211 A | 4/1987 | Sakamoto et al. |
| 4,672,969 A | 6/1987 | Dew |
| 4,675,117 A | 6/1987 | Neumann et al. |
| 4,680,025 A | 7/1987 | Kruger et al. |
| 4,714,457 A | 12/1987 | Alterbaum |
| 4,722,790 A | 2/1988 | Cawley et al. |
| 4,724,317 A | 2/1988 | Brown et al. |
| 4,735,616 A | 4/1988 | Eibl et al. |
| 4,735,726 A | 4/1988 | Duggins |
| 4,738,655 A | 4/1988 | Brimhall et al. |
| 4,755,300 A | 7/1988 | Fischel et al. |
| 4,755,301 A | 7/1988 | Bowers |
| 4,770,779 A | 9/1988 | Ichikawa et al. |
| 4,776,964 A | 10/1988 | Schoendorfer et al. |
| 4,818,291 A | 4/1989 | Iwatsuki et al. |
| 4,818,386 A | 4/1989 | Burns |
| 4,828,710 A | 5/1989 | Itoh et al. |
| 4,832,851 A | 5/1989 | Bowers et al. |
| 4,834,890 A | 5/1989 | Brown et al. |
| 4,839,058 A | 6/1989 | Cawley et al. |
| 4,844,818 A | 7/1989 | Smith |
| 4,846,780 A | 7/1989 | Galloway et al. |
| 4,846,835 A | 7/1989 | Grande |
| 4,846,974 A | 7/1989 | Kelley et al. |
| 4,850,952 A | 7/1989 | Figdor et al. |
| 4,853,137 A | 8/1989 | Ersson et al. |
| 4,871,462 A | 10/1989 | Fischel et al. |
| 4,874,368 A | 10/1989 | Miller et al. |
| 4,877,520 A | 10/1989 | Burns |
| 4,879,031 A | 11/1989 | Panzani et al. |
| 4,900,453 A | 2/1990 | Sedlmayer et al. |
| 4,902,281 A | 2/1990 | Avoy |
| 4,909,251 A | 3/1990 | Seelich et al. |
| 4,915,847 A | 4/1990 | Dillon et al. |
| 4,917,801 A | 4/1990 | Luderer et al. |
| 4,928,603 A | 5/1990 | Rose et al. |
| 4,929,242 A | 5/1990 | Desecki et al. |
| 4,933,291 A | 6/1990 | Daiss et al. |
| 4,939,081 A | 7/1990 | Figdor et al. |
| 4,943,273 A | 7/1990 | Pages et al. |
| 4,946,601 A | 8/1990 | Fiehler |
| 4,950,220 A | 8/1990 | Wells et al. |
| 4,957,637 A | 9/1990 | Cornell |
| 4,957,638 A | 9/1990 | Smith |
| 4,983,157 A | 1/1991 | Pober et al. |
| 4,983,158 A | 1/1991 | Headley |
| 4,985,153 A | 1/1991 | Kuroda et al. |
| 5,000,970 A | 3/1991 | Shanbhag et al. |
| 5,002,571 A | 3/1991 | O'Donnell, Jr. et al. |
| 5,019,243 A | 5/1991 | McEwen et al. |
| 5,024,613 A | 6/1991 | Vasconcellos et al. |
| 5,030,215 A | 7/1991 | Morse et al. |
| 5,030,341 A | 7/1991 | McEwen et al. |
| 5,039,401 A | 8/1991 | Columbus et al. |
| 5,045,048 A | 9/1991 | Kaleskas et al. |
| 5,047,004 A | 9/1991 | Wells |
| 5,053,127 A | 10/1991 | Schoendorfer et al. |
| 5,053,134 A | 10/1991 | Luderer et al. |
| 5,071,570 A | 12/1991 | Shiraki et al. |
| 5,080,262 A | 1/1992 | Herold et al. |
| 5,086,784 A | 2/1992 | Levine et al. |
| 5,100,564 A | 3/1992 | Pall et al. |
| 5,104,375 A | 4/1992 | Wolf et al. |
| 5,112,484 A | 5/1992 | Zuk, Jr. |
| 5,112,490 A | 5/1992 | Turpen |
| 5,131,907 A | 7/1992 | Williams et al. |
| 5,137,832 A | 8/1992 | Levine et al. |
| 5,141,645 A | 8/1992 | Shiraki et al. |
| 5,147,290 A | 9/1992 | Jonsson et al. |

| | | | | | |
|---|---|---|---|---|---|
| 5,152,905 A | 10/1992 | Pall et al. | 5,618,663 A | 4/1997 | Delmas et al. |
| 5,156,613 A | 10/1992 | Sawyer | 5,632,895 A | 5/1997 | Tsukagoshi et al. |
| 5,165,938 A | 11/1992 | Knighton | 5,632,905 A | 5/1997 | Haynes |
| 5,171,456 A | 12/1992 | Hwang et al. | 5,641,414 A | 6/1997 | Brown |
| 5,173,295 A | 12/1992 | Wehling et al. | 5,641,622 A | 6/1997 | Lake et al. |
| 5,178,602 A | 1/1993 | Wells | 5,643,192 A | 7/1997 | Hirsh et al. |
| 5,185,001 A | 2/1993 | Galanakis | 5,643,193 A | 7/1997 | Papillon et al. |
| 5,188,583 A | 2/1993 | Guigan et al. | 5,645,540 A | 7/1997 | Henniges et al. |
| 5,190,057 A | 3/1993 | Sarfarazi | 5,646,004 A | 7/1997 | Van Vlasselaer |
| 5,190,759 A | 3/1993 | Lindblad et al. | 5,648,223 A | 7/1997 | Van Vlasselaer |
| 5,197,985 A | 3/1993 | Caplan et al. | 5,649,903 A | 7/1997 | Deniega et al. |
| 5,203,825 A | 4/1993 | Haynes et al. | 5,663,051 A | 9/1997 | Vlasselaer |
| 5,204,537 A | 4/1993 | Bennet et al. | 5,674,173 A | 10/1997 | Hlavinka et al. |
| 5,206,023 A | 4/1993 | Hunziker et al. | 5,707,331 A | 1/1998 | Wells et al. |
| 5,207,638 A | 5/1993 | Choksi et al. | 5,707,647 A | 1/1998 | Dunn et al. |
| 5,217,426 A | 6/1993 | Bacehowski et al. | 5,707,876 A | 1/1998 | Levine |
| 5,217,627 A | 6/1993 | Pall et al. | 5,716,616 A | 2/1998 | Prockop et al. |
| 5,219,328 A | 6/1993 | Morse et al. | 5,723,331 A | 3/1998 | Tubo et al. |
| 5,226,877 A | 7/1993 | Epstein | 5,724,988 A | 3/1998 | Dennehey et al. |
| 5,226,914 A | 7/1993 | Caplan et al. | 5,733,466 A | 3/1998 | Benebo et al. |
| 5,234,608 A | 8/1993 | Duff | 5,733,545 A | 3/1998 | Hood, III |
| 5,236,604 A | 8/1993 | Fiehler | 5,736,033 A | 4/1998 | Coleman et al. |
| 5,251,786 A | 10/1993 | Sarrine | 5,738,784 A | 4/1998 | Holm et al. |
| 5,258,126 A | 11/1993 | Pall et al. | 5,738,796 A | 4/1998 | Bormann et al. |
| 5,260,420 A | 11/1993 | Burnouf-Radosevich et al. | 5,750,025 A | 5/1998 | Holmes et al. |
| 5,269,927 A | 12/1993 | Fiehler | 5,750,658 A | 5/1998 | Coelho et al. |
| 5,271,852 A | 12/1993 | Luoma, II | 5,762,798 A | 6/1998 | Wenthold et al. |
| 5,279,825 A | 1/1994 | Wehling et al. | 5,785,700 A | 7/1998 | Olson |
| 5,281,342 A | 1/1994 | Biesel et al. | 5,786,217 A | 7/1998 | Tubo et al. |
| 5,290,552 A | 3/1994 | Sierra et al. | 5,788,662 A | 8/1998 | Antanavich et al. |
| 5,290,918 A | 3/1994 | Bui-Khac et al. | 5,792,344 A | 8/1998 | Holm |
| 5,298,171 A | 3/1994 | Biesel et al. | 5,795,489 A | 8/1998 | Holm et al. |
| 5,304,372 A | 4/1994 | Michalski et al. | 5,795,571 A | 8/1998 | Cederholm-Williams et al. |
| 5,316,674 A | 5/1994 | Pall et al. | 5,795,751 A | 8/1998 | Apel |
| 5,318,524 A | 6/1994 | Morse et al. | 5,811,094 A | 9/1998 | Caplan et al. |
| 5,318,782 A | 6/1994 | Weis-Fogh et al. | 5,811,151 A | 9/1998 | Hendriks et al. |
| 5,321,126 A | 6/1994 | van Dommelen et al. | 5,817,519 A | 10/1998 | Zelmanovic et al. |
| 5,322,620 A | 6/1994 | Brown et al. | 5,823,986 A | 10/1998 | Peterson |
| 5,330,974 A | 7/1994 | Pines et al. | 5,824,084 A | 10/1998 | Muschler |
| 5,344,752 A | 9/1994 | Murphy | 5,830,359 A | 11/1998 | Knight et al. |
| 5,354,483 A | 10/1994 | Furse | 5,833,866 A | 11/1998 | Brown |
| 5,370,802 A | 12/1994 | Brown | 5,834,418 A | 11/1998 | Brazeau et al. |
| 5,372,945 A | 12/1994 | Alchas et al. | 5,837,150 A | 11/1998 | Langley et al. |
| 5,376,263 A | 12/1994 | Fischel | 5,840,502 A | 11/1998 | Van Vlasselaer |
| 5,387,187 A | 2/1995 | Fell et al. | 5,853,600 A | 12/1998 | McNeal et al. |
| 5,393,674 A | 2/1995 | Levine et al. | 5,860,937 A | 1/1999 | Cohen |
| 5,395,923 A | 3/1995 | Bui-Khac et al. | 5,863,892 A | 1/1999 | Stern et al. |
| 5,403,272 A | 4/1995 | Deniega et al. | 5,865,785 A | 2/1999 | Bischof |
| 5,405,607 A | 4/1995 | Epstein | 5,885,239 A | 3/1999 | Headley et al. |
| 5,409,833 A | 4/1995 | Hu et al. | 5,889,584 A | 3/1999 | Wardlaw |
| 5,411,885 A | 5/1995 | Marx | 5,895,346 A | 4/1999 | Wells et al. |
| 5,417,650 A | 5/1995 | Gordon | 5,899,874 A | 5/1999 | Jonsson et al. |
| 5,420,250 A | 5/1995 | Lontz | 5,900,245 A | 5/1999 | Sawhney et al. |
| 5,443,481 A | 8/1995 | Lee | 5,906,934 A | 5/1999 | Grande et al. |
| 5,454,958 A | 10/1995 | Fiehler | 5,916,557 A | 6/1999 | Berlowitz-Tarrant et al. |
| 5,456,693 A | 10/1995 | Conston et al. | 5,916,743 A | 6/1999 | Lake et al. |
| 5,456,885 A | 10/1995 | Coleman et al. | 5,918,622 A | 7/1999 | Perez et al. |
| 5,474,687 A | 12/1995 | Van Vlasselaer | 5,924,972 A | 7/1999 | Turvaville et al. |
| 5,480,378 A | 1/1996 | Weis-Fogh et al. | 5,934,803 A | 8/1999 | Hutter |
| 5,484,383 A | 1/1996 | Fitch, Jr. et al. | 5,938,621 A | 8/1999 | Kelly et al. |
| 5,486,359 A | 1/1996 | Caplan et al. | 5,955,032 A | 9/1999 | Kelly et al. |
| 5,494,578 A | 2/1996 | Brown et al. | 5,955,436 A | 9/1999 | Kunkle, Jr. |
| 5,494,592 A | 2/1996 | Latham, Jr. et al. | 5,958,250 A | 9/1999 | Brown et al. |
| 5,501,371 A | 3/1996 | Schwartz-Feldman | 5,958,253 A | 9/1999 | Holm et al. |
| 5,505,685 A | 4/1996 | Antwiler | 5,980,734 A | 11/1999 | Itoh et al. |
| 5,510,102 A | 4/1996 | Cochrum | 5,980,757 A | 11/1999 | Brown et al. |
| 5,520,885 A | 5/1996 | Coelho et al. | 5,985,315 A | 11/1999 | Patat et al. |
| 5,525,477 A | 6/1996 | Hassouna | 6,007,811 A | 12/1999 | Sawyer et al. |
| 5,533,518 A | 7/1996 | Vogler | 6,010,627 A | 1/2000 | Hood, III |
| 5,560,830 A | 10/1996 | Coleman et al. | 6,011,490 A | 1/2000 | Tonnesen et al. |
| 5,575,778 A | 11/1996 | Hardt et al. | 6,020,196 A | 2/2000 | Hu et al. |
| 5,577,513 A | 11/1996 | Van Vlasselaer | 6,022,306 A | 2/2000 | Dumont et al. |
| 5,585,007 A | 12/1996 | Antanavich et al. | 6,025,201 A | 2/2000 | Zelmanovic et al. |
| 5,588,958 A | 12/1996 | Cunningham et al. | 6,027,655 A | 2/2000 | Holm |
| 5,589,462 A | 12/1996 | Patat et al. | 6,049,026 A | 4/2000 | Muschler |
| 5,601,727 A | 2/1997 | Bormann et al. | 6,051,146 A | 4/2000 | Green et al. |
| 5,603,845 A | 2/1997 | Holm | 6,051,147 A | 4/2000 | Bischof |
| 5,607,579 A | 3/1997 | Latham, Jr. et al. | 6,053,856 A | 4/2000 | Hlavinka |
| 5,614,106 A | 3/1997 | Payrat et al. | 6,054,122 A | 4/2000 | MacPhee et al. |

| | | | | | | |
|---|---|---|---|---|---|---|
| 6,063,297 | A | 5/2000 | Antanavich et al. | 7,223,346 B2 | 5/2007 | Dorian et al. |
| 6,063,624 | A | 5/2000 | Kandler et al. | 7,273,886 B2 | 9/2007 | Olivero et al. |
| 6,071,421 | A | 6/2000 | Brown | 7,354,515 B2 | 4/2008 | Coull et al. |
| 6,071,422 | A | 6/2000 | Hlavinka et al. | 7,374,678 B2 | 5/2008 | Leach et al. |
| 6,071,423 | A | 6/2000 | Brown et al. | 7,411,006 B2 | 8/2008 | Shanbrom |
| 6,090,793 | A | 7/2000 | Zimmermann et al. | 7,470,371 B2 | 12/2008 | Dorian et al. |
| 6,096,309 | A | 8/2000 | Prior et al. | 7,531,355 B2 | 5/2009 | Rodriguez et al. |
| 6,102,843 | A | 8/2000 | Kelley et al. | 7,553,413 B2 | 6/2009 | Dorian et al. |
| 6,117,425 | A | 9/2000 | MacPhee et al. | 7,694,828 B2 | 4/2010 | Swift et al. |
| 6,123,655 | A | 9/2000 | Fell et al. | 7,806,276 B2 * | 10/2010 | Leach et al. .................. 210/516 |
| 6,150,163 | A | 11/2000 | McPherson et al. | 7,845,499 B2 * | 12/2010 | Higgins et al. ............. 210/380.1 |
| 6,153,113 | A | 11/2000 | Goodrich et al. | 7,901,584 B2 | 3/2011 | Dorian et al. |
| 6,183,737 | B1 | 2/2001 | Zaleske et al. | 7,914,689 B2 | 3/2011 | Higgins et al. |
| 6,196,987 | B1 | 3/2001 | Holmes et al. | 7,987,995 B2 | 8/2011 | Dorian et al. |
| 6,197,325 | B1 | 3/2001 | MacPhee et al. | 8,048,321 B2 | 11/2011 | Leach et al. |
| 6,200,287 | B1 | 3/2001 | Keller et al. | 8,062,534 B2 | 11/2011 | Higgins et al. |
| 6,200,606 | B1 | 3/2001 | Peterson et al. | 2001/0009757 A1 | 7/2001 | Bischof et al. |
| 6,214,338 | B1 | 4/2001 | Antanavich et al. | 2002/0032112 A1 | 3/2002 | Pages |
| 6,221,315 | B1 | 4/2001 | Giesler et al. | 2002/0035820 A1 | 3/2002 | Farris |
| 6,245,900 | B1 | 6/2001 | Yamasaki et al. | 2002/0076400 A1 | 6/2002 | Katz et al. |
| 6,264,890 | B1 | 7/2001 | Boehringer et al. | 2002/0082220 A1 | 6/2002 | Hoemann et al. |
| 6,274,090 | B1 | 8/2001 | Coelho et al. | 2002/0090711 A1 | 7/2002 | Karlsson |
| 6,277,961 | B1 | 8/2001 | Hock et al. | 2002/0104808 A1 | 8/2002 | Blasetti et al. |
| 6,280,400 | B1 | 8/2001 | Niermann | 2002/0114775 A1 | 8/2002 | Pathak |
| 6,296,602 | B1 | 10/2001 | Headley | 2002/0161449 A1 | 10/2002 | Muschler |
| 6,316,247 | B1 | 11/2001 | Katz et al. | 2002/0169408 A1 | 11/2002 | Beretta et al. |
| 6,322,785 | B1 | 11/2001 | Landesberg et al. | 2002/0172666 A1 | 11/2002 | Sacchi et al. |
| 6,327,491 | B1 | 12/2001 | Franklin et al. | 2002/0182664 A1 | 12/2002 | Dolecek et al. |
| 6,328,765 | B1 | 12/2001 | Hardwick et al. | 2002/0192632 A1 | 12/2002 | Hei et al. |
| 6,334,842 | B1 | 1/2002 | Hlavinka et al. | 2003/0033021 A1 | 2/2003 | Plouhar et al. |
| 6,342,157 | B1 | 1/2002 | Hood, III | 2003/0033022 A1 | 2/2003 | Plouhar et al. |
| 6,351,659 | B1 | 2/2002 | Vilsmeier | 2003/0050709 A1 | 3/2003 | Noth et al. |
| 6,355,239 | B1 | 3/2002 | Bruder et al. | 2003/0050710 A1 | 3/2003 | Petersen et al. |
| 6,368,298 | B1 | 4/2002 | Beretta et al. | 2003/0082152 A1 | 5/2003 | Hedrick et al. |
| 6,368,498 | B1 | 4/2002 | Guilmette | 2003/0185803 A1 | 10/2003 | Kadiyala et al. |
| 6,398,972 | B1 | 6/2002 | Blasetti et al. | 2003/0191429 A1 | 10/2003 | Andrew et al. |
| 6,406,671 | B1 | 6/2002 | DiCesare et al. | 2003/0205538 A1 | 11/2003 | Dorian et al. |
| 6,410,344 | B1 | 6/2002 | Chung et al. | 2004/0013575 A1 | 1/2004 | Stevens et al. |
| 6,417,004 | B1 | 7/2002 | Brady et al. | 2004/0120942 A1 | 6/2004 | McGinnis et al. |
| 6,440,444 | B2 | 8/2002 | Boyce et al. | 2004/0171146 A1 | 9/2004 | Katz et al. |
| 6,444,228 | B1 | 9/2002 | Baugh et al. | 2004/0182395 A1 | 9/2004 | Brookman |
| 6,464,624 | B2 | 10/2002 | Pages | 2004/0182788 A1 | 9/2004 | Dorian et al. |
| 6,471,069 | B2 | 10/2002 | Lin et al. | 2004/0182795 A1 | 9/2004 | Dorian et al. |
| 6,472,162 | B1 | 10/2002 | Coelho et al. | 2004/0251217 A1 | 12/2004 | Leach et al. |
| 6,487,992 | B1 | 12/2002 | Hollis | 2005/0076396 A1 | 4/2005 | Katz et al. |
| 6,508,778 | B1 | 1/2003 | Verkaart et al. | 2005/0084961 A1 | 4/2005 | Hedrick et al. |
| 6,516,953 | B1 | 2/2003 | DiCesare et al. | 2005/0084962 A1 | 4/2005 | Simon |
| 6,523,698 | B1 | 2/2003 | Dennehey et al. | 2005/0109716 A1 | 5/2005 | Leach et al. |
| 6,544,162 | B1 | 4/2003 | Van Wie et al. | 2005/0130301 A1 | 6/2005 | McKay et al. |
| 6,544,727 | B1 | 4/2003 | Hei | 2005/0145187 A1 | 7/2005 | Gray |
| 6,558,341 | B1 | 5/2003 | Swisher | 2005/0153441 A1 | 7/2005 | Hedrick et al. |
| 6,563,953 | B2 | 5/2003 | Lin et al. | 2005/0153442 A1 | 7/2005 | Katz et al. |
| 6,596,180 | B2 | 7/2003 | Baugh et al. | 2005/0186120 A1 | 8/2005 | Dorian et al. |
| 6,623,959 | B2 | 9/2003 | Harris | 2005/0196393 A1 | 9/2005 | Shanbrom |
| 6,629,919 | B2 | 10/2003 | Egozy et al. | 2005/0196874 A1 | 9/2005 | Dorian et al. |
| 6,638,503 | B2 | 10/2003 | Chitte et al. | 2005/0247715 A1 | 11/2005 | Ellsworth et al. |
| 6,676,629 | B2 | 1/2004 | Andrew et al. | 2005/0260174 A1 | 11/2005 | Fraser et al. |
| 6,719,901 | B2 | 4/2004 | Dolecek et al. | 2005/0260175 A1 | 11/2005 | Hedrick et al. |
| 6,733,471 | B1 | 5/2004 | Ericson et al. | 2005/0282275 A1 | 12/2005 | Katz et al. |
| 6,758,978 | B1 | 7/2004 | Bedell | 2006/0051865 A1 | 3/2006 | Higgins et al. |
| 6,764,531 | B2 | 7/2004 | Hogan | 2006/0057693 A1 | 3/2006 | Simon |
| 6,777,231 | B1 | 8/2004 | Katz et al. | 2006/0083720 A1 | 4/2006 | Fraser et al. |
| 6,803,022 | B2 | 10/2004 | DiCesare et al. | 2006/0140923 A1 | 6/2006 | Evangelista et al. |
| 6,811,777 | B2 | 11/2004 | Mishra | 2006/0151384 A1 | 7/2006 | Ellsworth et al. |
| 6,830,762 | B2 | 12/2004 | Baugh et al. | 2006/0175242 A1 | 8/2006 | Dorian et al. |
| 6,835,353 | B2 | 12/2004 | Smith et al. | 2006/0175244 A1 | 8/2006 | Dorian et al. |
| 6,835,377 | B2 | 12/2004 | Goldberg et al. | 2006/0178610 A1 | 8/2006 | Nowakowski |
| RE38,730 | E | 4/2005 | Wells et al. | 2006/0196885 A1 | 9/2006 | Leach et al. |
| 6,899,813 | B2 | 5/2005 | Dolecek et al. | 2006/0243676 A1 | 11/2006 | Swift et al. |
| 6,905,612 | B2 | 6/2005 | Dorian et al. | 2006/0273049 A1 | 12/2006 | Leach et al. |
| 6,911,202 | B2 | 6/2005 | Amir et al. | 2006/0273050 A1 | 12/2006 | Higgins et al. |
| RE38,757 | E | 7/2005 | Wells et al. | 2006/0278588 A1 | 12/2006 | Woodell-May |
| 6,979,307 | B2 | 12/2005 | Beretta et al. | 2007/0034579 A1 | 2/2007 | Dorian et al. |
| 7,011,644 | B1 | 3/2006 | Andrew et al. | 2007/0036768 A1 | 2/2007 | Fraser et al. |
| 7,077,273 | B2 | 7/2006 | Ellsworth et al. | 2007/0075016 A1 | 4/2007 | Leach |
| 7,077,827 | B2 | 7/2006 | Greenfield | 2007/0208321 A1 | 9/2007 | Leach et al. |
| 7,155,288 | B2 | 12/2006 | Soykan et al. | 2008/0011684 A1 | 1/2008 | Dorian et al. |
| 7,179,391 | B2 | 2/2007 | Leach et al. | 2008/0164204 A1 | 7/2008 | Hatamian et al. |
| 7,195,606 | B2 | 3/2007 | Ballin | 2008/0173593 A1 | 7/2008 | Coull et al. |

| | | | |
|---|---|---|---|
| 2008/0193424 A1 | 8/2008 | McKale et al. | |
| 2008/0210645 A1 | 9/2008 | Coull et al. | |
| 2008/0217263 A1 | 9/2008 | Higgins et al. | |
| 2008/0217264 A1 | 9/2008 | Leach et al. | |
| 2008/0217265 A1 | 9/2008 | Leach et al. | |
| 2008/0268064 A1 | 10/2008 | Woodell-May | |
| 2008/0269762 A1 | 10/2008 | Simon et al. | |
| 2008/0283474 A1 | 11/2008 | Leach et al. | |
| 2008/0306431 A1 | 12/2008 | Yoo | |
| 2009/0014391 A1 | 1/2009 | Leach et al. | |
| 2009/0018313 A1 | 1/2009 | Shanbrom | |
| 2009/0101599 A1 | 4/2009 | Dorian et al. | |
| 2009/0192528 A1 | 7/2009 | Higgins et al. | |
| 2009/0220482 A1 | 9/2009 | Higgins et al. | |
| 2009/0236297 A1 | 9/2009 | Dorian et al. | |
| 2009/0250413 A1 | 10/2009 | Hoeppner | |
| 2009/0253566 A1 | 10/2009 | Chavarria | |
| 2009/0289014 A1 | 11/2009 | Hoeppner | |
| 2010/0055087 A1 | 3/2010 | Higgins et al. | |
| 2010/0140182 A1 | 6/2010 | Chapman et al. | |
| 2010/0186676 A1 | 7/2010 | Van Der Berg | |
| 2010/0206798 A1 | 8/2010 | Dorian et al. | |
| 2010/0256595 A1 | 10/2010 | Leach et al. | |
| 2010/0323870 A1 | 12/2010 | Leach et al. | |
| 2010/0324450 A1 | 12/2010 | Leach et al. | |
| 2011/0014705 A1 | 1/2011 | Leach et al. | |
| 2011/0020196 A1 | 1/2011 | Grippi et al. | |
| 2011/0021334 A1 | 1/2011 | Leach et al. | |
| 2011/0036786 A1 | 2/2011 | Ellsworth | |
| 2011/0056893 A1 | 3/2011 | Leach et al. | |
| 2011/0065183 A1 | 3/2011 | Dorian et al. | |
| 2011/0077596 A1 | 3/2011 | Higgins et al. | |
| 2011/0168193 A1 | 7/2011 | Leach et al. | |
| 2011/0192804 A1 | 8/2011 | Landrigan et al. | |
| 2011/0251041 A1 | 10/2011 | Chavarria et al. | |
| 2012/0015796 A1 | 1/2012 | Leach et al. | |

FOREIGN PATENT DOCUMENTS

| | | | |
|---|---|---|---|
| BR | 9103724 | | 3/1993 |
| CA | 1321138 | | 8/1993 |
| CA | 2182862 | | 6/1996 |
| CA | 2448415 | A1 | 12/2002 |
| CN | 1074709 | | 7/1993 |
| DE | 56103 | | 10/1860 |
| DE | 1443359 | | 11/1968 |
| DE | 4202667 | | 5/1993 |
| EP | 090997 | | 10/1983 |
| EP | 0102773 | | 3/1984 |
| EP | 0109374 | | 5/1984 |
| EP | 0142339 | | 5/1985 |
| EP | 0244834 | A2 | 11/1987 |
| EP | 0253198 | | 1/1988 |
| EP | 0272915 | A2 | 6/1988 |
| EP | 285891 | | 10/1988 |
| EP | 0295771 | | 12/1988 |
| EP | 0417818 | | 3/1991 |
| EP | 534178 | | 3/1993 |
| EP | 0534178 | | 3/1993 |
| EP | 0592242 | | 4/1994 |
| EP | 1005910 | | 6/2000 |
| EP | 1006360 | | 6/2000 |
| EP | 1289618 | | 3/2003 |
| EP | 1406492 | B1 | 4/2004 |
| EP | 1427279 | A1 | 6/2004 |
| EP | 1467746 | A2 | 10/2004 |
| EP | 1509326 | | 3/2005 |
| EP | 1670315 | A2 | 6/2006 |
| EP | 1716901 | A1 | 11/2006 |
| GB | 854715 | | 11/1960 |
| JP | 60-053845 | | 3/1985 |
| JP | 60250014 | | 12/1985 |
| JP | 63182055 | A | 7/1988 |
| JP | 6454256 | | 4/1989 |
| JP | 2036872 | | 2/1990 |
| JP | 02071747 | | 3/1990 |
| JP | 04500170 | T | 1/1992 |
| JP | 09187504 | A | 7/1997 |
| JP | 9509432 | T | 9/1997 |
| JP | 11502502 | T | 3/1999 |
| JP | 2000117150 | A | 4/2000 |
| JP | 02129224 | | 10/2000 |
| JP | 2001017540 | A | 1/2001 |
| JP | 2005523128 | T | 8/2005 |
| MX | 246078 | | 5/2007 |
| WO | WO-8400905 | | 3/1984 |
| WO | WO-8802259 | | 4/1988 |
| WO | WO-8901827 | A1 | 3/1989 |
| WO | WO-9010031 | | 9/1990 |
| WO | WO-9222312 | | 12/1992 |
| WO | WO-9305067 | | 3/1993 |
| WO | WO-9308904 | | 5/1993 |
| WO | WO-9407548 | | 4/1994 |
| WO | WO-9616714 | A1 | 6/1996 |
| WO | WO-9617871 | | 6/1996 |
| WO | WO-9848938 | | 11/1998 |
| WO | WO-0061256 | | 10/2000 |
| WO | WO-0074713 | A1 | 12/2000 |
| WO | WO-0103756 | | 1/2001 |
| WO | WO-0183068 | | 11/2001 |
| WO | WO-0224107 | | 3/2002 |
| WO | WO-0238610 | A1 | 5/2002 |
| WO | WO-02060925 | A1 | 8/2002 |
| WO | WO-02098566 | A2 | 12/2002 |
| WO | WO-03015800 | | 2/2003 |
| WO | WO-03024215 | A1 | 3/2003 |
| WO | WO-03053362 | A2 | 7/2003 |
| WO | WO-03088905 | | 10/2003 |
| WO | WO-03090839 | A1 | 11/2003 |
| WO | WO-03092894 | A2 | 11/2003 |
| WO | WO-03099412 | A1 | 12/2003 |
| WO | WO-2004009207 | | 1/2004 |
| WO | WO-2004037427 | A1 | 5/2004 |
| WO | WO-2004104553 | A2 | 12/2004 |
| WO | WO-2005034843 | A2 | 4/2005 |
| WO | WO-2006081699 | A1 | 8/2006 |
| WO | WO-2007127834 | A2 | 11/2007 |
| WO | WO-2007142908 | A1 | 12/2007 |
| WO | WO-2009021257 | A1 | 2/2009 |
| WO | WO 2009111338 | A1 * | 9/2009 |

OTHER PUBLICATIONS

Office Action mailed Apr. 6, 2010 for Japanese Application No. 2007-554193 filed Aug. 23, 2007 has been provided including a partial translation thereof, which cites JP11-502502 and JP2001017540. Japanese Application No. 2007-554193 claims benefit of PCT/US2006/003599, filed Jan. 30, 2006; claiming priority from U.S. Appl. No. 60/651,050, filed Feb. 7, 2005; U.S. Appl. No. 60/654,718, filed Feb. 17, 2005; and U.S. Appl. No. 60/723,312, filed Oct. 4, 2005 of which U.S. Appl. No. 11/831,605 filed Jul. 31, 2007 and U.S. Appl. No. 12/772,497, filed May 3, 2010 claim benefit.

Office Action mailed Apr. 6, 2010 for Japanese Application No. 2007554191 filed Aug. 7, 2007 has been provided including a partial translation thereof, which also cites JP2001017540. Japanese Application No. 2007554191 claims benefit of PCT/US2006/003597, filed Jan. 30, 2006; claiming priority from U.S. Appl. No. 60/651,050, filed Feb. 7, 2005; U.S. Appl. No. 60/654,718, filed Feb. 17, 2005; and U.S. Appl. No. 60/723,312, filed Oct. 4, 2005 of which U.S. Appl. No. 11/831,605, filed Jul. 31, 2007 and U.S. Appl. No. 12/772,497, filed May 3, 2010 claim benefit.

Office Action mailed Sep. 14, 2010 for Japanese Application No. 2007-554193 filed Aug. 23, 2007 has been provided including a partial translation thereof. Japanese Application No. 2007-554193 claims benefit of PCT/US2006/003599, filed Jan. 30, 2006; claiming priority from U.S. Appl. No. 60/651,050, filed Feb. 7, 2005; U.S. Appl. No. 60/654,718, filed Feb. 17, 2005; and U.S. Appl. No. 60/723,312, filed Oct. 4, 2005 of which U.S. Appl. No. 11/831,605, filed Jul. 31, 2007 and U.S. Appl. No. 12/772,497, filed May 3, 2010 claim benefit.

Office Action mailed Sep. 14, 2010 for Japanese Application No. 2007554191 filed Aug. 7, 2007 has been provided including a partial translation thereof. Japanese Application No. 2007554191 claims benefit of PCT/US2006/003597, filed Jan. 30, 2006; claiming priority from U.S. Appl. No. 60/651,050, filed Feb. 7, 2005; U.S. Appl. No. 60/654,718, filed Feb. 17, 2005; and U.S. Appl. No. 60/723,312, filed Oct. 4, 2005 of which U.S. Appl. No. 11/831,605, filed Jul. 31, 2007 and U.S. Appl. No. 12/772,497, filed May 3, 2010 claim benefit.

Jayadev, Suprya. "Trypsinization of Adherent Cells." Aug. 8, 1991. Web. Apr. 14, 2010 http://www.duke.edu/web/ceramide/protocols/0005.html.

Connolly, John, M.D., et al. "Development of an Osteogenic Bone-Marrow Preparation." The Journal of Bone and Joint Surgery, Incorporated. vol. 71-A, No. 5 (Jun. 1989) pp. 684-691.

Hom, D., et al. "Promoting Healing with Recombinant Human Platelet-Derived Growth Factor-BB in a Previously Irradiated Problem Wound." The Laryngoscope, vol. 113 (pp. 1566-1671) Sep. 2003.

DePalma, L., et al., "The preparation of fibrinogen concentrate for use as fibrin glue by four different methods." Transfusion (1993) vol. 33, No. 9; pp. 717-720.

Friesen, M.D., Robert, et al. "Blood Conservation During Pediatric Cardiac Surgery: Ultrafiltration of the Extracorporeal Circuit Volume After Cardiopulmonary Bypass." Anesth. Analg 1993: 77-702-7.

Hood, Andrew G., et al., "Perioperative Autologous Sequestration III: A New Physiologic Glue with Wound Healing Properties," (Jan. 1993) vol. 14 pp. 126-129.

International Preliminary Report on Patentability and Written Opinion mailed Oct. 13, 2011 for PCT/US2010/029957 which claims benefit of U.S. Appl. No. 12/417,789, filed Apr. 3, 2009.

Longas, Maria O., "An Improved Method for the Purification of Human Fibrinogen." J. Biochem (1980) vol. 11, pp. 559-564.

Marx, Gerard, et al., "Heat Denaturation of Fibrinogen to Develop a Biomedical Matrix." Journal of Biomedical Materials Research Part B: Applied Biomaterials (Apr. 2007) pp. 49-57.

Masri, Marwan A., et al. "Isolation of Human Fibrinogen of High Purity and in High Yield Using Polyethylene Glycol 1000." Thromb Haemostas (Struttgart) (1983) vol. 49 (2); pp. 116-119.

Orphardt, Charles E., "Denaturation of Proteins," Virtual Chembook, Elmhurst College (2003) 3 pages. http://www.elmhurst.edu/~chm/vchembook/568denaturation.html (web accessed Mar. 9, 2011).

Silver, Frederick H., et al., "Review Preparation and use of fibrin glue in surgery." Biomaterials 16 (1995) pp. 891-903.

Solem, Jan Otto, et al., "Hemoconcentration by Ultrafiltration During Open-Heart Surgery," Scand J Thor Cardiovasc Surg 22:271-274, 1988.

Sutton, Robin G., et al. "Comparison of Three Blood-Processing Techniques During and After Cardiopulmonary Bypass." Ann Thorac Surg (1993) vol. 56; pp. 941-943.

Weisman, MD., Robert A., "Biochemical Characterization of Autologous Fibrinogen Adhesive," Laryngoscope 97: Oct. 1987; pp. 1186-1190.

Badiavas, et al., "Treatment of Chronic Wounds With Bone Marrow-Derived Cells," (Reprinted) Arch Dermatol. 139:510-516 (Apr. 2003).

Connolly, "Injectable Bone Marrow Preparations to Stimulate Osteogenic Repair," Clinical Orthopaedics and Related Research 313:8-18 (1995).

De Ugarte, et al., "Comparison of Multi-Lineage Cells from Human Adipose Tissue and Bone Marrow," Cells Tissues Organs 174:101-109 (2003).

De Ugarte, et al., "Differential Expression of Stem Cell Mobilization-Associated Molecules on Multi-Lineage Cells from Adipose Tissue and Bone Marrow," Immunology Letters 89:267-270 (2003).

Eppley, et al., "Platelet Quantification and Growth Factor Analysis from Platelet-Rich Plasma: Implications for Wound Healing," Plastic and Reconstructive Surgery, 114(6):1502-1508 (Nov. 2004).

Floryan, K. et al. "Home Study Program: Intraoperative Use of Autologous Platelet-Rich and Platelet-Poor Plasma for Orthopedic Surgery Patients" vol. 80, No. 4 (Oct. 2004) p. 667-674.

Haynesworth, S.E. et al. "Mitogenic Stimulation of Human Mesenchymal Stem Cells by Platelet Releasate Suggests a Mechanism for Enhancement of Bone Repair by Platelet Concentrate" 48th Annual Meeting of the Orthopaedic Research Society Poster No. 0462 (2002).

Hernigou, et al., "Percutaneous Autologous Bone-Marrow Grafting for Nonunions. Influence of the Number and Concentration of Progenitor Cells," Journal of Bone & Joint Surgery, 87-A(7):1430-1437 (Jul. 2005).

International Preliminary Examination Report and Written Opinion issued Aug. 31, 2010 for PCT/US2009/035564 claiming benefit of U.S. Appl. No. 61/078,178, filed Jul. 3, 2008, which priority is also claimed of said provisional case by U.S. Appl. No. 12/395,085, filed Feb. 27, 2009.

International Search Report and Written Opinion mailed Jul. 30, 2010 for PCT/US2010/029957 which claims benefit of U.S. Appl. No. 12/417,789, filed Apr. 3, 2009.

Ishida, et al., "Platelet-Rich Plasma With Biodegradable Gelatin Hydrogel Promotes Rabbit Meniscal Tissue Regeneration," 52nd Annual Meeting of the Orthopaedic Research Society Paper No. 1035, 1 page (2006).

Johnstone, et al., "Autologous Mesenchymal Progenitor Cells in Articular Cartilage Repair", Clinical Orthopaedics and Related Research 367S:S156-S162 (1999).

Marrowstim Concentration System, Biomet Biologics, Inc., 20 pages (REV Feb. 15, 2008).

Woodell-May, et al., "Producing Accurate Platelet Counts for Platelet Rich Plasma: Validation of a Hematology Analyzer and Preparation Techniques for Counting," Scientific Foundation, Journal of Carniofacial Surgery 16(5):749-756 (Sep. 2005).

"Cell Isolation Techniques, Methods and Materials, Working with Enzymes," (2004) (9 pages) Worthington Biochemical Corp.

"Cell Isolation Theory, Tissue Types," (2004) (5 pages) Worthington Biochemical Corp.

"Cytori Celution Cell Concentrate Device," Exhibit 14, 510(k) Summary, FDA approval K060482 (Sep. 28, 2006).

"Frequently Asked Questions, 1. Kits, 2. Engzymes," (2003) 3 pages Worthington Biochemical Corp.

"Sefar Solutions for the Healthcare Industry," brochure (2003) 9 pages Sefar Medifab®.

"Trypsinization of Adherent Cells," (undated) 2 pages.

Anesthesiology, vol. 81, No. 4, pp. 1074-1077, Oct. 1994, Hiromasa Mitsuhata, M.D., et al., "An Anaphylactic Reaction to Topical Fibrin Glue".

Ann Thorac Surg, vol. 53, pp. 530-531, 1992, Mehmet C. Oz, M.D., et al., "Autologous Fibrin Glue From Intraoperatively Collected Platelet-Rich Plasma".

Ann Thorac Surg, vol. 56, pp. 387-389, 1993, Robert L. Quigley, M.D., et al., "Intraoperative Procurement of Autologous Fibrin Glue".

Bang, N.U., et al., "Plasma Protein Requirements for Human Platelet Aggregation" Ann. N.Y. Acad Sci, 201:280-299 (1972).

Berguer, R., R. L. Staerkel, E. E. Moore, F. A. Moore, W. B. Galloway, and M. B. Mockus. "Warning: fatal reaction to the use of fibrin glue in deep hepatic wounds. Case reports." J Trauma 31 (3 1991): 408-11.

Berruyer, M., J. Amiral, P. Ffrench, J. Belleville, O. Bastien, J. Clerc, A. Kassir, S. Estanove, and M. Dechavanne. "Immunization by bovine thrombin used with fibrin glue during cardiovascular operations. Development of thrombin and factor V inhibitors," J Thorac. Cardiovasc Surg 105 (5 1993):892-7.

Biopolymers, vol. 27, pp. 763-774, 1988, Gerald Marx, "Mechanism of Fibrin Coagulation Based on Selective, Cation-Driven, Protofibral Association".

Brodke, et al., "Bone Grafts Prepared with Selective Cell Retention Technology Heal Canine Segmental Defects as Effectively as Autograft", SCR-Enriched Bone Crafts Heal Canine Segmental Defects, Journal of Orthopaedic Research (May 2006) pp. 857-866.

Casali, B., F. Rodeghiero, A. Tosetto, B. Palmieri, R. Immovilli, C. Ghedini, and P. Rivasi. "Fibrin glue from single-donation autologous plasmapheresis." Transfusion 32 (Jul. 1992): 641-3.

CLOTALYST™ Automatic Clotting Factor, Would you like to have an autologous thrombin for rapid clotting and haemostasis?, brochure, Biomet Biologics, Inc., Feb. 2007 (12 pages).

Collier, B.S. et al., "The pH Dependence of Quantitative Ristocetin-induced Platelet Aggregation: Theoretical and Practical Implications—A New Device for Maintenance of Platelet-Rich Plasma pH", Hematology Service, Clinical Pathology Department, Clinical Center, National Institutes of Health, Bethesda, MD. 20014, Blood, vol. 47, No. 5 (May), 1976.

Dallari, et al., "In Vivo Study on the Healing of Bone Defects Treated with Bone Marrow Stromal Cells, Platelet-Rich Plasma, and Freeze- Dried Bone Allografts, Alone and in Combination," Healing of Bone Defects, Journal of Orthopaedic Research (May 2006) pp. 877-888.

DelRossi, A. J., A. C. Cemaianu, R. A.Vertrees, C. J. Wacker, S. J. Fuller, J. Cilley Jr., and W. A. Baldino. "Platelet-rich plasma reduces postoperative blood loss after cardiopulmonary bypass." *J Thorac Cardiovasc Surg* 100 (2 1990): 281-6.

DeUgarte, M.D., Daniel A., et al., "Future of Fat as Raw Material for Tissue Regneration," (2007) pp. 215-219, Lippincott Williams & Wilkins, Inc.

DiMuzio, Paul et al., "Development of a Tissue-Engineered Bypass Graft Seeded with Stem Cells," Vasucular, vol. 14, No. 6, (2006) pp. 338-342, BC Decker, Inc.

Drug Intelligence and Clinical Pharmacy, vol. 22, pp. 946-952, Dec. 1988, Dennis F. Thompson, et al., "Fibrin Glue: A Review of Its Preparation, Efficacy, and Adverse Effects as a Topical Hemostat".

Edlich, Richard F., George T. Rodeheaver, and John G. Thacker. "Surgical Devices in Wound Healing Management." In *Wound Healing: Biochemical & Clinical Aspects*, ed. I. Kelman Cohen, Robert F. Diegelmann, and William J. Lindblad. 581-600. 1st ed., vol. Philadelphia: W.B. Saunders Company, 1992).

Epstein, G. H., R. A. Weisman, S. Zwillenberg, and A. D. Schreiber. "A new autologous fibrinogen-based adhesive for otologic surgery." *Ann Otol Rhinol Laryngol* 95 (1 Pt 1 1986): 40-5.

Fibrostik™ Plasma Concentrator, Attention Operating Surgeon, Cell Factor Technologies, Inc., Jul. 2003.

First clinical results: Kuderma, H. and Helene Matras. "Die klinische Anwendung der Klebung van Nervenanastomosen mit Gerinnungssubstanzen bei der Rekonstruction verletzter peripherer Nerven." Wein Klin Wochenschr 87 (15 1975): 495-501.

Frasier, John K., et al., "Plasticity of human adipose stem cells toward endothelial cells and cardiomyocytes," Nature Clinical Practice Cardiovascular Medicine, vol. 3, Supplement 1 (Mar. 2006) pp. S33-S37.

Galois, et al., "Cartilage Tissue Engineering: State-of-the-Art and Future Approaches," Pathol Biol (Paris), 53(10), Dec. 2005.

Gibble, J. W. and P. M. Ness. "Fibrin glue: the perfect operative sealant?" *Transfusion* 30 (8 1990): 741-7.

Gimble, Jeffrey M., "Adipose-Derived Stem Cells for Regenerative Medicine," Circulation Research (2007) pp. 1249-1260, American Heart Association, Inc.

Gomillion, Cheryl T., et al., "Stem cells and adipose tissue engineering," Biomaterials 27, Science Direct (2006) pp. 6052-6063, Elsevier.

GPS® III System, GPS® III Platelet Separation System, Leadership through Technology, brochure, Jul. 2007 (8 sheets).

GPS® System, "GPS® Platelet Concentrate System," Cell Factor Technologies, Inc, Biomet Orthopaedics, Inc., (2004) (9 pages).

GPS® System, "Shoulder Recovery with the GPS® Platelet Concentrate System, Rotator Cuff Surgical Techniques," brochure, Cell Factor Technologies, Inc., Biomet Orthopaedics, Inc., (2004) 6 pages.

GPS® System, "Shoulder Recovery with the GPS® Platelet Concentrate System, Rotator Cuff Surgical Techniques," Cell Factor Technologies, Inc., Biomet Orthopaedics, Inc., (2004) 3 pages, http://www.cellfactortech.com/global_products.cfm, printed Sep. 16, 2005.

GPS® II System, Gravitational Platelet Separation System, "Accelerating the Body's Natural Healing Process," Cell Factor Technologies, Inc., Biomet Europe (2005) 16 pages, http://www.cellfactortech.com/global_products.cfm, printed Sep. 16, 2005.

GPS® II System, Gravitational Platelet Separation System, "User Manual," Cell Factor Technologies, Inc., Biomet Europe [date unknown] 13 pages, http://www.cellfactortech.com/global_products.cfm, printed Sep. 16, 2005.

Grove, et al., "Plasticity of Bone Marrow-Derived Stem Cells," Stem Cells: Concise Review, Jan. 22, 2004.

Guilak, Frank, et al., "Adipose-derived adult stem cells for cartilage tissue engineering," Biorheology 41 (2004) pp. 389-399, IOS Press.

Harris, E.L.V. Concentration of the Extract. In. Protein Purification Methods: A Practical Approach Harris, E.L.V.; Angal, S.; Editors. (1989) Publisher: (IRL Press, Oxford, UK), pp. 67-69.

Hartman, A. R., D. K. Galanakis, M. P. Honig, F. C. Seifert, and C. E. Anagnostopoulos. "Autologous whole plasma fibrin gel. Intraoperative procurement." *Arch Surg* 127 (Mar. 1992): 357-9.

Harvest SmartPrep PRP-20 Procedure Pack, "Instructions for Use".

Harvest Technologies brochure, SmartPrep2 (2002).

Hattori, et al., "Osteogenic Potential of Human Adipose Tissue-Derived Stromal Cells as an Alternative Stem Cell Source," Cells Tissues Organs (2004) 178:2-12 Karger.

Hennis, H. L., W. C. Stewart, and E. K. Jeter. "Infectious disease risks of fibrin glue [letter]." *Ophthalmic Surg* 23 (Sep. 1992): 640.

International Preliminary Report on Patentability completed Aug. 13, 2009 for PCT/US2008/004687 claiming benefit of U.S. Appl. No. 60/911,407, filed Apr. 12, 2007.

International Preliminary Report on Patentability mailed Feb. 12, 2009, for PCT/US2007/017055 filed Jul. 31, 2007, which claims benefit of U.S. Appl. No. 60/834,550, filed Jul. 31, 2006, based on U.S. Appl. No. 60/723,312, filed Oct. 4, 2005; U.S. Appl. No. 60/654,718, filed Feb. 17, 2005; and U.S. Appl. No. 60/651,050, filed Feb. 7, 2005.

International Search Report and Written Opinion for PCT/US2006/003597 mailed Feb. 6, 2006.

International Search Report and Written Opinion for PCT/US2006/003599 mailed Aug. 21, 2006.

International Search Report and Written Opinion mailed Aug. 12, 2008 for PCT/US07/17055.

International Search Report and Written Opinion mailed Jul. 2, 2008 for International Application No. PCT/US2008/004687 which claims priority to U.S. Appl. No. 60/911,407, filed Apr. 12, 2007.

International Search Report and Written Opinion mailed Jul. 3, 2009 for PCT/US2009/035564 claiming benefit of U.S. Appl. 61/078,178, filed Jul. 3, 2008.

International Search Report for International Application No. PCT/US0316506 mailed Oct. 13, 2003 which claims benefit of U.S. Appl. No. 60/383,013, filed May 24, 2002.

International Search Report for International Application No. PCT/US2007/012587 mailed Nov. 6, 2007 which claims benefit of U.S. Appl. No. 11/441,276, filed May 25, 2006.

Jackson, C. M. and Y. Nemerson. "Blood coagulation." *Annu Rev Biochem* 49 (811 1980): 765-811).

Jorgensen, et al., "Stem Cells for Repair of Cartilage and Bone: The Next Challenge in Osteoarthritis and Rheumatoid Arthritis," Annals of Rheumatic Diseases, Aug. 2000.

Journal of Biomaterials Applications, vol. 7, pp. 309-353, Apr. 1993, David H. Sierra, "Fibrin Sealant Adhesive Systems: A review of their Chemistry, Material Properties and Clinical Appllications".

Journal of Oral Maxillofacial Surgery, vol. 43, pp. 605-611, 1985, Helene Matras, M.D., "Fibrin Seal: The State of the Art".

Karpatkin, S., "Heterogeneity of Human Platelets. VI., Correlation of Platelet Function with Platelet Volume", Blood, vol. 51, No. 2 (Feb. 1978).

Kjaergard, H. K,, U. S. Weis-Fogh, H. Sorensen, J. Thiis, and I. Rygg. "A simple method of preparation of£ autologous fibrin glue by means of ethanol." *Surg Gynecol Obstet* 175 (Jan. 1992): 72-3.

Kjaergard, H. K., Fogh Us Weis, and J. J. Thiis. "Preparation of autologous fibrin glue from pericardial blood." *Ann Thorac Sur* 55 (Feb. 1993): 543-4.

Laryngoscope vol. 99, pp. 974-976, Sep. 1989, Kyosti Laitakari, M.D., et al., "Autologous and Homologous Fibrinogen Sealants: Adhesive Strength".

Laryngoscope, vol. 95, pp. 1074-1076, Sep. 1985, Karl H. Siedentop, M.D., et al., "Autologous Fibrin Tissue Adhesive".

Laryngoscope, vol. 96, pp. 1062-1064, Oct. 1986, Karl H. Siedentop, M.D., et al., "Extended Experimental and Preliminary Surgical Findings with Autologous Fibrin Tissue Adhesive Made from Patient's Own Blood".

Lasher, Lisa, M.D., "My Experience with PRP," PowerPoint presentation, http://www.cellfactortech.com/global_products.cfm, printed Sep. 16, 2005.

Lendeckel, Stefan, et al., "Autologous stem cells (adipose) and fibrin glue used to treat widespread traumatic calvarial defects: case report," Journal of Cranio-Maxillofacial Surgery (2004) European Association for Cranio-Maxillofacial Surgery.

Lemer, R. and N. S. Binur. "Current status of surgical adhesives." *J Surg Res* 48 (Feb. 1990): 165-81.

Lu, et al., "Bone Marrow Mesenchymal Stem Cells: Progress in Bone/Cartilage Defect Repair," 19(1), Jan. 2002.

Marrowstim™ Concentration System, (2008) 20 pages Biomet Biologics, Inc.

Matras, Helene, H. P. Dinges, H. Lassmann, and B. Mamoli. "Zur nahtlosen interfaszikularen Nerventransplantation im Tierexperiment." Wein Med Woschtr 122 (37 1972): 517-523.

Minntech® Filtration Technologies Group, "Hemocor HPH® Hemoconcentrator," Minntech Corporation (2004); http://www.minntech.com/ftg/products/hph/index.html, printed Jul. 15, 2004 (2 pages).

Minntech® Filtration Technologies Group, "Medical Applications: Blood Filtration" Minntech Corporation (2004); http://www.minntech.com/ftg/industries/medical/blood_filter.html, printed Jul. 15, 2004 (1 page).

Minntech® Filtration Technologies Group, "Renaflo® II Hemofilter," Minntech Corporation (2004); http://www.minntech.com/ftg/products/renaflo/index.html, printed Jul. 15, 2004 (2 pages).

Molnar, Amy, "Stem Cells from Muscles Can Repair Cartilage, Study Finds Genetically Engineered Muscle-Derived Stem Cells Improved Cartilage Repair in Rats", American College of Rheumatology, (2005).

Moretz, W., Jr., J Shea Jr., J. R. Emmett, and J Shea. "A simple autologous fibrinogen glue for otologic surgery." *Otolaryngol Head Neck Surg* 95 (Jan. 1986): 122-4.

Nakagami, Hironori, et al., "Novel Autologous Cell Tehrapy in Ischemic Limb Disease Through Growth Factor Secretion by Cultured Adipose Tissue-Derived Stromal Cells," Angiogenesis by Adipose Tissue-Derived Cells, (2005) pp. 2542-2547, American Heart Association, Inc.

Nathan, Suresh et al., "Cell-Based Therapy in the Repair of Osteochondral Defects: A Novel Use for Adipose Tissue," Tissue Engineering, vol. 9, No. 4 (2003) pp. 733-744 Mary Ann Liebert, Inc.

Nilsson, et al., "Bone Repair Induced by Bone Morphogenetic Protein in Ulnar Defects in Dogs," The Journal of Bone and Joint Surgery, vol. 68 B., No. 4, Aug. 1986.

Otolaryngologic Clinics of North America, vol. 27, No. 1, pp. 203-209, Feb. 1994, Dean M. Toriumi, M.D., et al., "Surgical Tissue Adhesives in Otolaryngology—Head and Neck Surgery".

Parker, Anna M., et al., Adipose-derived stem cells for the regeneration of damaged tissues, Expert Opinion, Cell- & Tissue-based Therapy, Expert Opin. Biol. Ther. (2006) pp. 567-578 Informa UK Ltd.

Planat-Bénard, V., et al., "Spontaneous Cardiomyocyte Differentiation From Adipose Tissue Stroma Cells," Adipose-Derived Cell Cardiomyocyte (2004) pp. 223-229 American Heart Association, Inc.

Plasmax™ Plasma Concentrate, brochure (2006) 5 pages Biomet Biologics, Inc.

Ponticiello, Michael S., "A Rapid Technique for the Isolation and Concentration of Stem Cells from Human Bone Marrow", Cell Factor Technologies, Inc. (undated) 1 page.

Rangappa, Sunil, M.D., "Transformation of Adult Mesenchymal Stem Cells Isolated From the Fatty Tissue Into Cardiomyocytes," Adult Stem Cells Transformed into Cardiomyoctyes, (2003) pp. 775-779 Ann Thorac Surg.

Rigotti, M.D., et al, "Clinical Treatment of Radiotherapy Tissue Damage by Lipoaspirate Transplant: A Healing Process Mediated by Adipose-Derived Adult Stem Cells," Plastic and Reconstructive Surgery, Breast, PRS Journal vol. 119, No. 5, Stem Cell Therapy for Angiogenesis, (Pub. 2005) pp. 1409-1422.

Rubin, M.D., et al, "Clinical Treatment of Radiotherapy Tissue Damage by Lipoaspirate Transplant: A Healing Process Mediated by Adipose-Derived Adult Stem Cells," Plastic and Reconstructive Surgery, Discussion vol. 119, No. 5, Stem Cell Therapy for Angiogenesis, (2007) pp. 1423-1424.

Sanal, M. "Does fibrin glue cause foreign body reactions? [letter]." *Eur J Pediatr Surg* 3 (Mar. 1993): 190 (1 page).

Sanal, M., H. Dogruyol, A. Gurpinar, and O. Yerci. "Does fibrin glue cause foreign body reactions?" *Eu r J Pediatr Surg* 2 (May 1992): 285-6.

Schmidt, K.G., et al., "Labelling of Human and Rabbit Platelets with Indium-Oxine Complex", 23:97-106 (1979).

Schmidt, K.G., et al., "Preparation of Platelet Suspensions from Whole Blood in Buffer", Scand. J. Hoemato, 23:88-96 (1979).

Schäffler, Andreas, et al., "Concise Review: Adipose Tissue-Derived Stromal Cells—Basic and Clinical Implications for Novel Cell-Based Therapies," Tissue-Specific Stem Cells, Stem Cells® (2007) pp. 818-827 AlphaMed Press.

Sierra, D. H. "Fibrin sealant adhesive systems: a review of their chemistry, material properties and clinical applications." *J Biomater Appl* 7 (Apr. 1993): 309-52.

Sigma-Aldrich® Alkaline Phosphatase (Procedure No. 85), drug fact sheet, (2003) pp. 1-2, Sigma-Aldrich, Inc.

Swift, Mathew J., et al., "Characterization of Growth Factors in Platelet Rich Plasma," 1-Cell Factor Technologies, http://www.cellfactortech.com/global_products.cfm, printed Sep. 16, 2005.

Symphony II Platelet Concentrate System/PCS brochure; "Increasing bone graft bioactivity through reproducible concentrations of natural growth factors," DePuy (Jan. 2003).

Takahashi, Kazutoshi et al., "Induction of Pluripotent Stem Cells from Adult Human Fibroblasts by Defined Factors," Cell, (2007) pp. 1-12, Elsevier Inc.

The American Journal of Surgery, vol. 168, pp. 120-122, Aug. 1994, Roy L. Tawes, Jr., M.D., et al., "Autologous Fibrin Glue: The Last Step in Operative Hemostatis".

The American Surgeon, vol. 55, pp. 166-168, Mar. 1989, William D. Spotnitz, M.D., et al., "Successful Use of Fibrin Glue During 2 Years of Surgery at a University Medical Center".

The Sports Medicine Center, "Knee Cartilage Implantation", Carticel™, "Autologous Cultured Chondrocyte Implantation", http://www.orthoassociates.com/carticel.htm (printed Apr. 6, 2006).

The Stone Clinic, "Platelet Rich Plasma (PRP)", web site printed May 2006.

Vortech™ Concentration System, "Do you want a sticky gel to improve the handling of your bone graft?, Platelet Rich Plasma Concentrate, High Volume in 5 Minutes," Biomet Biologics, Inc., Aug. 2005.

Vox Sanquinis, vol. 68: 82-89, Feb. 1995, Boomgaard Et. al, Pooled Platelet Concentration Prepred by the . . . .

Weis-Fogh, U. S. "Fibrinogen prepared from small blood samples for autologous use in a tissue adhesive system." *Eur Surg* Res 20 (May-Jun. 1988): 381-9.

Wiseman, David M., David T. Rovee, and Oscar M. Alverez. "Wound Dressings: Design and Use." In *Wound Healing: Biochemical & Clinical Aspects*,ed. I. Kelman Cohen, Robert F. Diegelmann, and William J. Lindblad. 562-580. 1st ed., vol. Philadelphia: W. B. Saunders Company, 1992).

Written Opinion of the International Preliminary Examining Authority mailed Mar. 17, 2009 for International Application No. PCT/US2008/004687 which claims priority to U.S. Appl. No. 60/911,407, filed Apr. 12, 2007.

Yoon, Eulsik, M.D., Ph.D., et al., "In Vivo Osteogenic Potential of Human Adipose-Derived Stem Cells/Poly Lactide-Co-Glycolic Acid Constructs for Bone Regneration in a Rat Critical-Sized Calvarial Defect Model," Tissue Engineering, vol. 13, No. 3 (2007) pp. 619-627 Mary Ann Liebert, Inc.

Zhang, Duan-zhen, et al., "Transplantation of autologous adipose-derived stem cells ameliorates cardiac function in rabbits with myocardial infarction," Chinese Medical Journal, vol. 120, No. 4 (2007) pp. 300-307 General Hospital of Shenyang Military Region, Shenyang, China.

Zuk, Patricia A., Ph.D., "Multilineage Cells from Human Adipose Tissue: Implications for Cell-Based Therapies," Tissue Engineering, vol. 7, No. 2, (2001) pp. 211-228 Mary Ann Liebert, Inc.

"Caps for Corning® and Costar® Plastic Labware," Technical Bulletin. (Dec. 2008) Corning, Incorporated.

"Centrifuge Tubes" Corning Costar brochure. 1996/1997 Catalog pp. 76-77.

"Clotalyst® Autologous Clotting Factor" brochure. (Aug. 15, 2008) Biomet Biologics.

"Clotalyst® Autologous Clotting Factor. Would you like to have an autologous thrombin for rapid clotting and haemostasis?" Brochure. Biomet Biologics (Aug. 15, 2008).

"Corning® 15 and 50 mL Centrifuge Tubes," Life Sciences. (Jun. 2005) Corning Incorporated.

"Letter CryoSeal FS System. Vaccines, Blood & Biologics," letter. (Jul. 26, 2007) FDA U.S. Food and Drug Administration. http://www.fda.gov/BiologicsBloodVaccines/BloodBloodProducts/ApprovedProducts/PremarketApprovalsPMAs/ucm091631.htm (Web accessed Aug. 12, 2011).

"MarrowStim™ Concentration Kit Peripheral Arterial Disease (PAD) Study" brochure. Web. Jul. 2, 2009 http://www.biomet.com/patients/clinical_recruitment_padstudy.cfm.

"MarrowStim™ Concentration System," brochure. Biomet Biologics Jun. 15, 2008.

"Plasmax® Plasma Concentration System" brochure. (Jun. 15, 2008) Biomet® Biologics.

"Prosys PRP Kit," brochure Tozai Holdings, Inc. http://tozaiholdings.en.ec21.com/Prosys_PRP_Kit—5467051_5467061.html Printed from Web Aug. 24, 2011.

"Prosys PRP Kit," Tozai Holdings, Inc. EC21 Global B2B Marketplace http://www.ec21.com/product-details/Prosys-PRP-Kit—5467061.html Printed from Web Jul. 18, 2011.

"ThermoGenesis Corp. to Supply Autologous Thrombin Kits to Biomet, Inc.," PR Newslink: http:/tinyurl.com/4h3up. (Apr. 5, 2005) http://www.noblood.org/press-releases/2128-thermogenesis-corp-supply-autologous-thrombin-kits-biomet-inc [web accessed Sep. 27, 2011].

GPS® II System, Gravitational Platelet Separation System, "Accelerating the Body's Natural Healing Process," Biomet Biologics (Jul. 15, 2006) 16 pages.

International Preliminary Report on Patentability mailed Jan. 26, 2012 for PCT/US2010/041942 claiming benefit of U.S. Appl. No. 12/504,413, filed Jul. 16, 2009.

International Search Report and Written Opinion mailed Aug. 9, 2011 for PCT/US2011/031954 claiming benefit of U.S. Appl. No. 12/758,127, filed Apr. 12, 2010.

International Search Report and Written Opinion mailed Nov. 7, 2011 for PCT/US2011/045290 claiming benefit of U.S. Appl. No. 12/846,944, filed Jul. 30, 2010.

International Search Report and Written Opinion mailed Oct. 8, 2010 for PCT/US2010/041942 claiming benefit of U.S. Appl. No. 12/504,413, filed Jul. 16, 2009.

Kumar, Vijay et al. "Stability of Human Thrombin Produced From 11 ml of Plasma Using the Thrombin Processing Device," Journal of American Society of Extra-Corporeal Technology. JECT: Mar. 2005:37; 390-395.

Kumar, Vijay et al. "Whole Blood Thrombin: Development of a Process for Intra-Operative Production of Human Thrombin." Journal of American Society of Extra-Corporeal Technology. JECT: Apr. 2007; 39:18-23.

Kumar, Vijay et al., "Autologous Thrombin: Intraoperative Production From Whole Blood." Journal of American Society of Extra-Corporeal Technology. JECT: Apr. 2008; 40:94-98.

Semple, Elizabeth, PhD, et al. "Quality of Thrombin Produced From the Patient's Own Plasma Using the TPD™, a New Thrombin-Processing Device." Journal of American Society of Extra-Corporeal Technology. JECT: 2005; 37:196-200.

Sanal, M. "Does fibrin glue cause foreign body reactions? [letter]." *Eur J Pediatr Surg* 3 (1992): 190 (1 page).

Rigotti, M.D., et al, "Clinical Treatment of Radiotherapy Tissue Damage by Lipoaspirate Transplant: A Healing Process Mediated by Adipose-Derived Adult Stem Cells," Plastic and Reconstructive Surgery, Breast, PRS Journal vol. 119, No. 5, Stem Cell Therapy for Angiogenesis, (Apr. 15, 2007) pp. 1409-1422.

DeUgarte, M.D., Daniel A., et al., "Future of Fat as Raw Material for Tissue Regeneration," (Feb. 2003) pp. 215-219, Lippincott Williams & Wilkins, Inc.

* cited by examiner

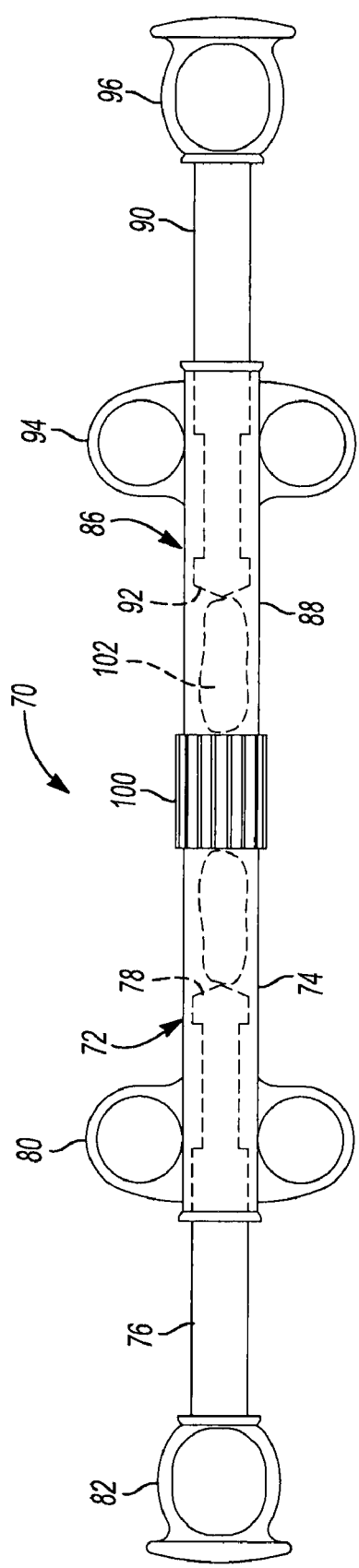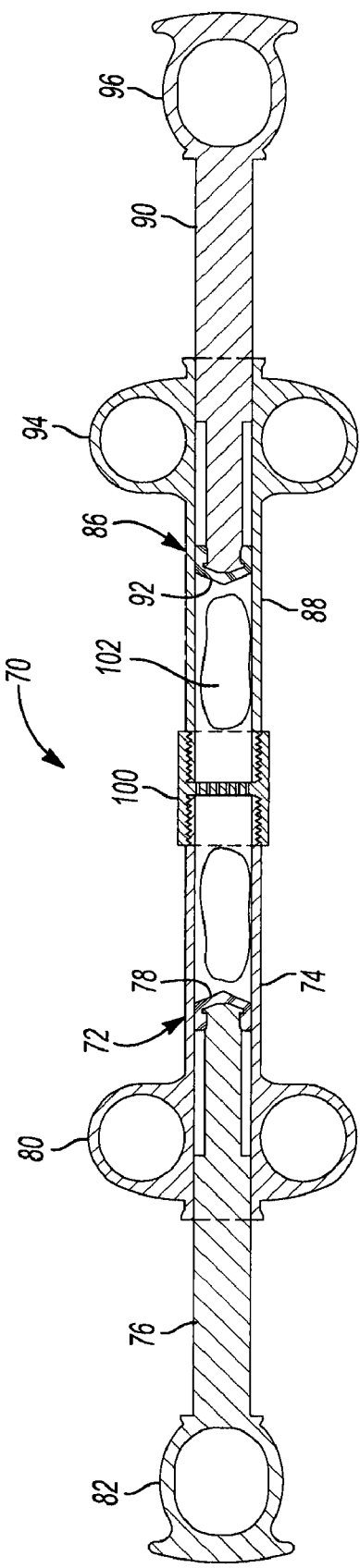

SYSTEM AND PROCESS FOR SEPARATING A MATERIAL

CROSS-REFERENCE TO RELATED APPLICATIONS

This application claims the benefit of both U.S. Provisional Application No. 61/032,619, filed on Feb. 29, 2008 and U.S. Provisional Application No. 61/078,178, filed on Jul. 3, 2008. The disclosures of the above applications are incorporated herein by reference.

FIELD

The present disclosure relates generally to separation of a selected component from a multi-component biological material.

BACKGROUND

The statements in this section merely provide background information related to the present disclosure and may not constitute prior art.

Various cellular (or biological) materials can be used to assist a person in a healing or recovery process. Pluripotent cells, multi-potent cells, stem cells, or fully differentiated cells can be applied to a patient for providing therapy to the patient. For example, stem cells can be applied to a patient to assist in healing an affected area through differentiation of the stem cells. In addition, stem cells can be applied to an area of the patient that may be damaged due to injury, chemotherapy, or radiation therapy to assist in regeneration of the affected cells.

Stem cells can be acquired from various sources. Selected sources can include autologous sources, where the patient is a donor or self donor. The autologous source of the stem cells can include various tissues, such as adipose tissue. Adipose tissue can be used as a source of cells, such as stem cells or vascular endothelial cells that can be separated, concentrated, or purified from the fat cells.

SUMMARY

A selected cell population from a selected tissue sample, such as adipose tissue, can be separated, enriched, and/or purified. The selected cell population can include pluripotent, multipotent, or stem cells or other cells having therapeutic value for use in a therapy. The population can be collected via aspiration or excision of a tissue sample and further processed for separation and purification of the selected cells from the tissue sample. Therapeutic non-cellular material (for example extracellular matrix) can also be separated and purified. The tissue sample can include adipose tissue, mucosa, muscle, blood, or other appropriate tissue sources.

The tissue sample can be acquired from a patient and separated in an efficient and time effective manner for application to the same patient (i.e. autologous). Use of autologous cells can reduce possible rejection and reduce contamination issues. Further, autologous cells can provide a genetic match to the patient.

A process for acquiring a tissue sample, according to various embodiments, can generally include aspirating or excising adipose tissue from a patient. The aspirated or excised adipose tissue can then be disrupted, macerated, and/or pulverized. The disrupted tissue can then be separated using a separation system as discussed herein. In the separation system, the disrupted tissue can be suspended in a selected biologically acceptable solution that can aid in separation or enrichment of a selected fraction of cells.

A system for separating the selected fraction of cells from the tissue sample can include a container that is operable to rotate around a central axis so that the tissue sample is moved towards or pressed against an outer wall (such as centrifugal forces) and separated based upon size and/or density. Areas of different size or density can be formed between the central axis and the outer wall. The separation device can also have a separate concentric ring or collection area that can collect a selected fraction of the material, such as a selected cell fraction, and a closure valve for the collection area. Disruption devices, according to various embodiments, including those discussed herein, can be used to disrupt the tissue sample prior to the separation of the selected fraction in a separation system.

Although the present disclosure may refer to aspirate or lipoaspirate, it will be understood that any appropriate tissue sample may be used, unless specifically indicated otherwise. For example, muscle or mucosa tissue can be excised, disrupted, and separated as discussed herein. In addition, adipose tissue may also be excised rather than only aspirated.

In addition, a selected fraction, such as a selected cell fraction, can include stem cells. It will be understood, however, that stem cells can be used herein, unless otherwise specified, to indicate cells that are undifferentiated or incompletely differentiated and able to differentiate into more than one cell type. For example, a stem cell may be able to differentiate, depending upon various factors, into one or more distinct cells. Certain populations of cells, however, may only differentiate into one, two, or any discrete number of cell types. Also, a selected fraction can include cells that are unlimited or limited in their differentiation possibilities. Undifferentiated cells can also include pluripotent or multipotent cells. These cells can differentiate into an appropriate number of cell types.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 3A is a plan view of a tissue disrupter, according to various embodiments;

FIG. 3B is a cross-sectional view of the disrupter of the FIG. 3A;

DETAILED DESCRIPTION

The following description is merely exemplary in nature and is not intended to limit the present disclosure, application, or uses.

Figure 1:
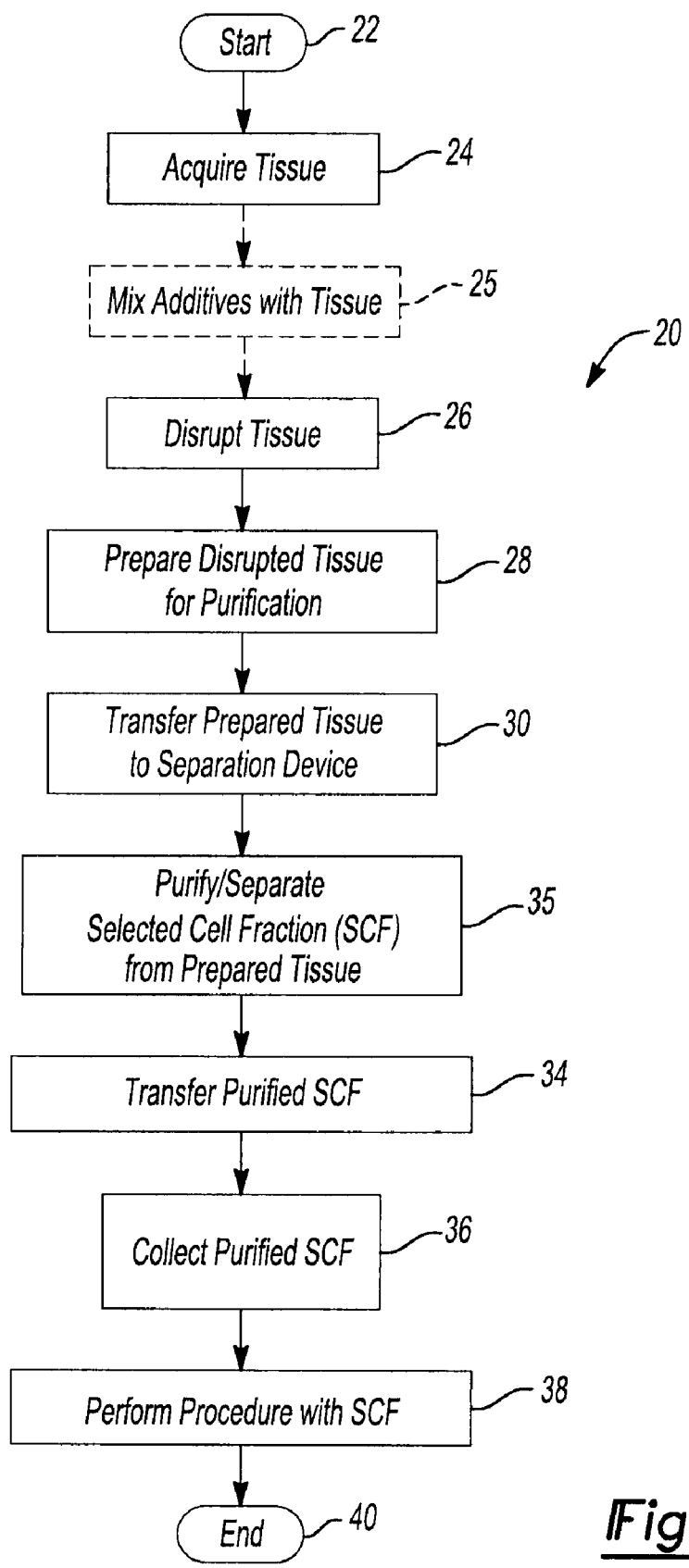
FIG. 1 is a flowchart illustrating a general process for tissue separation.

With reference to FIG. 1, a flow chart 20 illustrates a general process of acquiring a selected fraction of cells from a tissue sample. A selected fraction can include a cell population, such as stem cells or other undifferentiated cell populations, as discussed above. According to various embodiments, the process starts at Start block 22. Any appropriate tissue sample, (e.g. adipose tissue) can be acquired in block 24. If the selected tissue is adipose tissue, it can be acquired in various techniques, such as during liposuction, aspirating adipose tissue from a selected source, or other appropriate techniques. For example, during a prosthesis implantation, adipose tissue can be excised or removed from the patient near or at the incision for the prosthesis implantation. Therefore, aspiration of tissue is merely an exemplary process for withdrawing or removing tissue from a patient.

The tissue sample can be mixed or suspended with an appropriate additive in optional block 25. Additives can include materials to adjust pH or for chelating, such as citrate. A pH can be selected to be about 4 to about 9, and can be selected to be about 4 to about 6. Other additives can include lytic activity materials (for example, RBC lysis buffer), ion channel blockers, anti-apoptosis agents, protease inhibitors, density modifiers, chaotropic agents, osmolarity altering agents (to differentially alter density and/or fragility of sub-populations of cells), and/or detergents. These additives can alter pH, chelate various ions, etc. The additives, however, generally are enzyme free. Thus, enzymes are generally not, and need not be added to the tissue sample. In addition, any additive is optional and may not be added until the tissue sample is prepared for separation after processing. The solution or the tissue can be maintained at about 35 to 45 degrees centigrade (C).

The tissue can be disrupted in block 26. The disruption of the tissue can occur according to any appropriate technique or with any appropriate device, including those described further herein and may include adding additives, as described above. Nevertheless, the disruption of the tissue can generally be performed to obtain a selected cluster or particle size of the tissue. For example, it may be selected to obtain clusters of tissue (including cells and intercellular matrix) that are about 0.1 mm to about 5 mm, in size including about 0.5 mm to about 2 mm, and also including about 1 mm in average size. It will be understood that clusters of tissue may not be perfect spheres or other geometric shapes and therefore the average size can include a diameter dimension, a size defined by random measurement, a sieve measurement, or any other appropriate measurement, such as microscopy, coulter counting, laser light scattering and other techniques well known to those skilled in the art. In addition, an adipose tissue sample can be disrupted to about 0.5 mm to about 2 mm, including about 1 mm in average cluster size.

A selected cell fraction or population can be prepared for separation from the tissue sample in block 28. The tissue can be suspended in a selected suspension material or otherwise prepared for separation. For example, a chelating agent, such as citrate, can be mixed with the disrupted tissue. The citrate, or other chelating agent, can weaken the bonds between cells, cells and an extracellular matrix, and between cells, the extracellular matrix, and other components in the extracellular matrix. Thus, citrate or other appropriate materials can assist in separation of a selected cell fraction. Further, citrate or other similar materials, such as chelating compounds, can assist or enhance separation without the addition of enzymes.

In addition, the solution can be maintained or provided at a selected pH for purification or separation. It will be understood, the addition of an acid or a base can be used to acquire a selected pH. Also, the addition of various materials, such as the citrate, can alter or be used to provide a selected pH of the material for separation.

The tissue can be suspended in a solution to assist with separation. For example, the tissue can be placed in an intermediate density solution (e.g. Ficoll® copolymers sold by GE HEALTHCARE BIO-SCIENCES AB of SWEDEN) where adipose tissues can rise. The combination of the intermediate density solution and tissue can also be centrifuged, as discussed further herein. Centrifugation with an additional solution, in addition to the tissue, is not necessary.

Other additives can also be added for various purposes as discussed above. Materials, however, need not be added. This is true regardless of whether a material has already been added.

Once the tissue has been prepared for purification, the tissue can be placed into a separation or purification device in block 30. Placing the tissue sample in the device in block 30 can include transferring the tissue cells and any additive materials previously added. It will be understood that additives need not be provided. The transfer of the prepared tissue to the separation device in block 30 can be performed in any appropriate manner. For example, the material can be transferred in a syringe (e.g. sterile syringe), a transfer container, a sterile syringe, or any appropriate technique. Various transport systems can include those disclosed in U.S. patent application Ser. No. 11/222,303, filed Sep. 8, 2005, now U.S. Pat. No. 7,766,900, commonly assigned, and incorporated herein by reference.

The selected cell fraction can then be separated in block 32. The separation of the selected cell fraction can occur according to various embodiments, including those discussed further herein. For example, the GPS™ separation system, sold by Biomet Inc. of Warsaw, Ind., USA can be used to separate the selected cell fraction from tissue. Exemplary buoy separation systems are disclosed in U.S. patent application Ser. No. 10/932,882, filed on Sep. 2, 2004, now U.S. patent application Ser. No. 7,374,678, incorporated herein by reference. The buoy or separation device can be designed with an appropriate density or specific gravity for stem cell separation from adipose tissue, or other appropriate separations. Further, separation devices can include those discussed further herein.

The purified selected cell fraction can be transferred in block 34, according to various embodiments, automatically or manually to a selected or isolation area. For example, a separation device can be used that includes a separation area and a collection area where the purified selected cell fraction is collected substantially automatically during a separation process. Therefore, the transfer of the purified cells in block 34 is optional and other collection techniques can be used. Regardless, a collection of the selected cell fraction occurs in block 36. The selected cell fraction that is purified can be collected in any appropriate manner, as discussed further herein. In block 38, an optional procedure can be performed with the selected cell fraction. Accordingly, the procedure may end at END block 40 after collecting the purified selected cell fraction with or without performing a procedure with the collected cells. Nevertheless, a selected procedure can be performed, such as applying the selected cell fraction to a patient or using the selected cell fraction in a selected therapeutic procedure. It will be understood, however, that the selected cell fraction can also be used for various other procedures, such as research, seeding a scaffold (i.e., building an ex-vivo structure), cell line creation, and the like.

Figure 2:
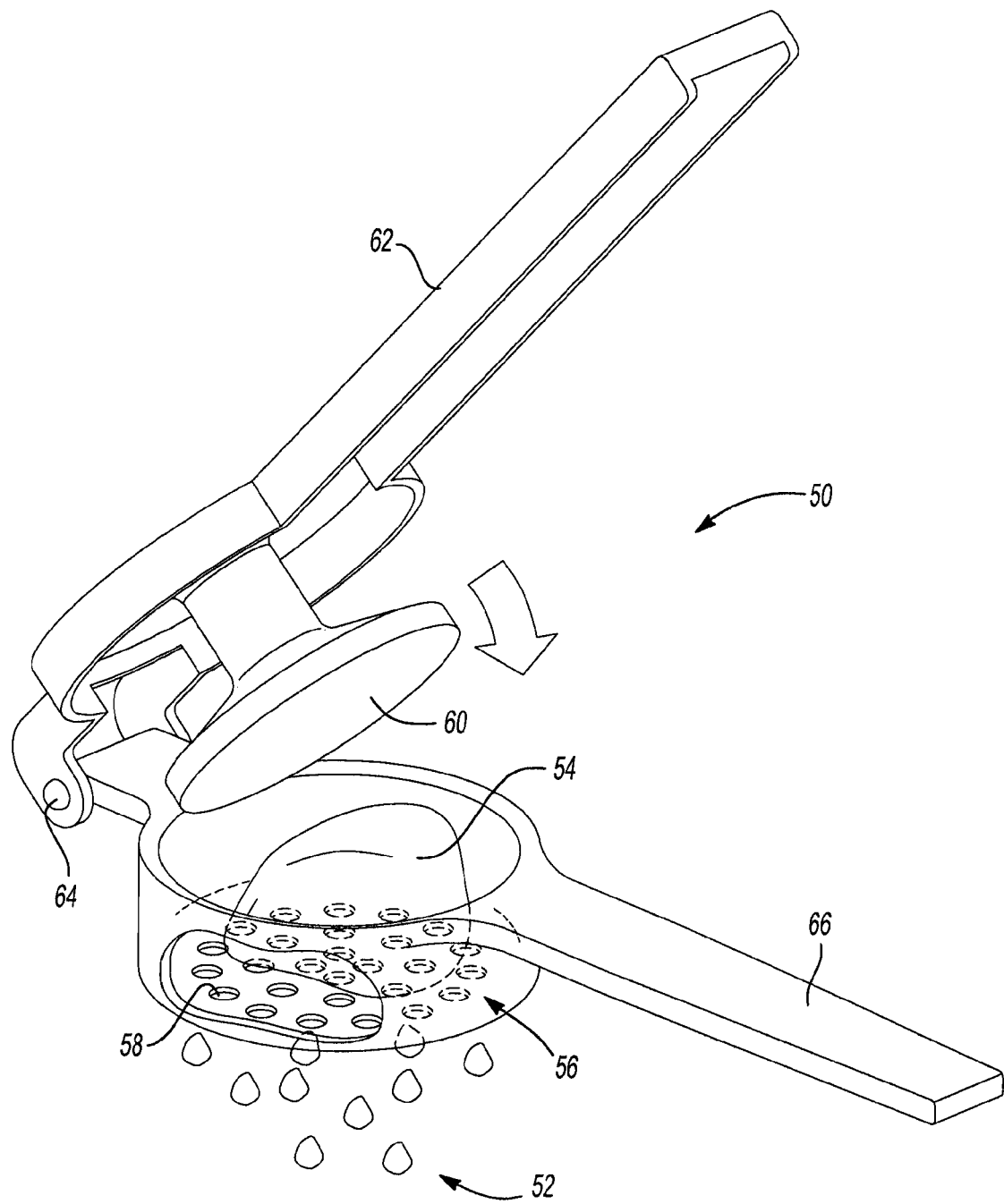
FIG. 2 is a perspective view of a tissue disrupter, according to various embodiments.

With reference to FIG. 2, a disruption device can include a mechanical press 50. The mechanical disruption device 50 can be used to create disrupted tissue 52 from aspirated or collected tissue 54. The mechanical disruption device 50 can include a collection area 56 into which the initially collected tissue 54, collected according to various appropriate procedures, is placed. The collection area 56 can include a frit or screen 58 through which the undisrupted tissue can be forced to create the disrupted tissue 52. The undisrupted tissue 54 can be forced through the frit 58 with a press portion 60 that is adapted or configured to fit within the collection 56 and force the undisrupted tissue 54 through the frit 58. A mechanical force can be applied to a lever arm 62 to which the press portion 60 is connected to force the undisrupted tissue 54 through the frit 58. A fulcrum 64 can interconnect the lever arm 62 of the press portion 60 with a second arm 66 which can define or be connected with the collection area 56. After disruption, the disrupted tissue 52 can be processed according to the method 20, illustrated in FIG. 1, and further herein. It will be understood that the tissue can include an adipose tissue sample.

With reference to FIGS. 3A-4B, a dual syringe or reciprocating syringe and disruption frit assembly 70 is illustrated. The dual syringe system can include a first syringe assembly 72 including a cylinder 74 defining a wall and an interior and a piston rod and/or plunger 76. The piston rod 76 with the syringe assembly 72 can terminate in a plunger or stopper member 78. To assist in reciprocation or movement of the plunger 78, the syringe assembly 72 can include finger holds or holding members 80 connected with the cylinder 74 and a second finger grasping portion 82 interconnected with the rod 76.

A second syringe assembly 86 can be provided also including a cylinder 88 and a rod portion 90 that terminates in a plunger 92. Similar grasping portions 94, 96 can be interconnected with a cylinder 88 and rod 90. The two syringes can be interconnected with a frit member 100. The two syringe assemblies 72 and 86 can be used to move a sample 102 through the frit assembly 100 between the two cylinder bodies 74, 88. The movement through the frit assembly 100 can disrupt the adipose tissue in a defined manner.

Figure 4A:
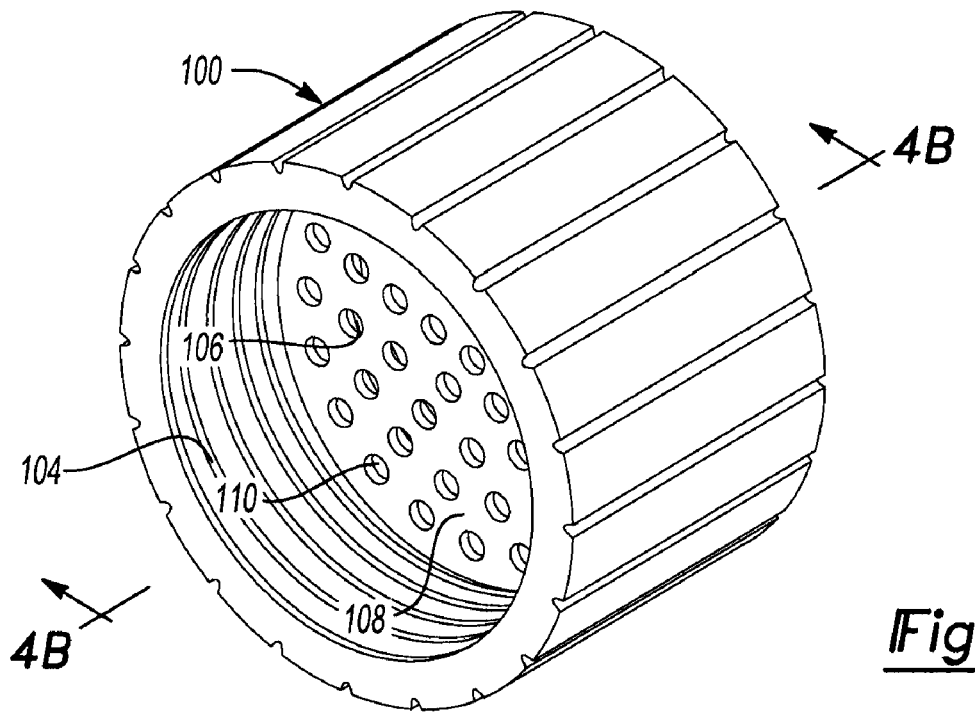
FIG. 4A is a frit assembly, according to various embodiments.
Figure 4B:
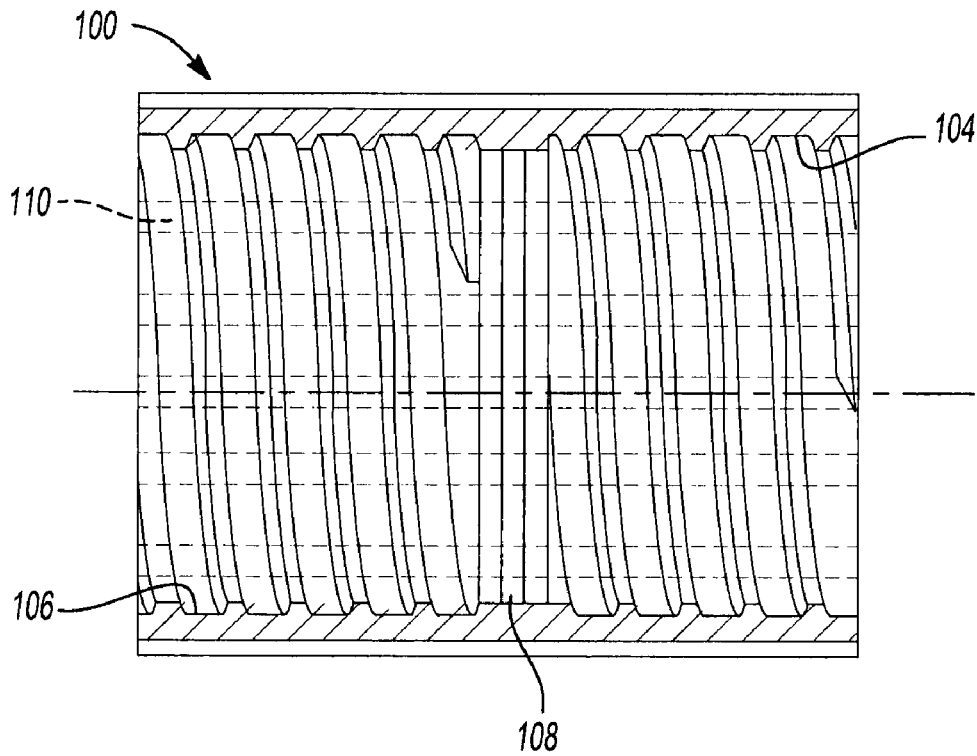
FIG. 4B is a plan and transparent view of the assembly of FIG. 4A.

With reference to FIG. 4A, 4B, the frit assembly 100 can include two threaded portions; a first threaded portion 104 and a second threaded portion 106. The two threaded portions 104, 106 of the frit assembly 100 allow the first syringe assembly 72 and the second syringe assembly 86 to engage a threaded coupling the frit assembly 100. It will be understood that other coupling mechanisms, such as a friction or interference fit, can be provided to couple the syringes to the frit assembly 100. Thus, the first and second syringe assemblies 72, 86 can be selectively connected with the frit assembly 100. This can also be used to allow for loading or unloading of the tissue sample. For example, one or both of the syringe assemblies 72, 86 can be disconnected from the frit assembly 100 and the tissue sample can be loaded into one or both of the syringe assemblies. As discussed further herein, the syringe assemblies 72, 86 can then be used to reciprocate the tissue sample through the frit member 108 to disrupt the tissue sample, as discussed further herein.

A frit member or body 108 can include one or more throughbores or passages 110 that allow material to pass, such as tissue, as the two syringe assemblies 72, 86 are used to reciprocate the sample through the frit body 108. The sample is forced through the holes 110 with the syringe assemblies 72, 86. The reciprocation mechanically disrupts the tissue and an appropriate number of reciprocations can occur to achieve a selected disruption of the tissue sample. Furthermore, the holes 110 in the frit body 108 can be provided in any appropriate dimension, such as a diameter, to achieve a selected disruption of the fat. Therefore, a dual or reciprocating syringe assembly 70 can also be used to disrupt the tissue sample in block 26 of the method 20. Again, the tissue sample can include an adipose tissue sample from an appropriate source.

The holes 110 defined in the frit body 108 can include any appropriate dimension. For example, the frit holes can include a dimension of about 0.02 inches to about 1 inch, including about 0.04 inches to about 0.5 inches, such as about 0.25 inches. The dimension of the holes 110 can be any appropriate dimension and may vary depending upon the cell type to be enriched or concentrated from the tissue sample. Also, the hole size can be provided according to the source of the tissue sample to be disrupted. For example, a lipoaspirate originated sample may be disrupted with a smaller opening to achieve a selected particle size as opposed to a sample from another source, such as a sample from an abdominoplasty.

Moreover, a kit including a plurality of the frit assemblies 100 can include multiple frit bodies with different holes of different dimensions. Therefore, a user can select an appropriate frit dimension depending upon the source of the adipose tissue. Moreover, an adipose tissue that is being disrupted can be moved through a plurality of frit assemblies. The kit can include a plurality of the frit assemblies 100 including hole dimensions that may be progressively smaller so that the adipose sample can be moved through progressively smaller hole dimensions to progressively increase disruption of the fat or adipose tissue sample. For example, as discussed above, a first frit assembly 100 including a first selected hole dimension can be interconnected with both of the syringe assemblies 72, 86. The tissue sample can be disrupted by reciprocating the syringe assemblies 72, 86 and after a selected period of time or cycles of reciprocation, the first frit assembly can be replaced with a second frit assembly having holes 110 of a different dimension. The syringe assemblies 72, 86 can then be reciprocated to disrupt the tissue with the different hole dimension size for a selected period of time or number of cycles. This can be repeated until selected tissue sample particle size or disruption size has been achieved.

According to various embodiments, a single syringe, as opposed to a dual syringe, with an appropriate frit assembly can also be used for disruption. A single syringe can operate similarly to the duel syringe, save that the material can be expressed through the frit to a collection container or area. In addition, the frit assembly, according to various embodiments, can include a single passage or orifice for disruption. Examples of a single orifice frit can include an aspiration needle. Various embodiments can include single plungers, as discussed herein, with various mechanical assist mechanisms. Various frits of differing passage diameters can be provided for appropriate disruption of the sample.

Figure 5:
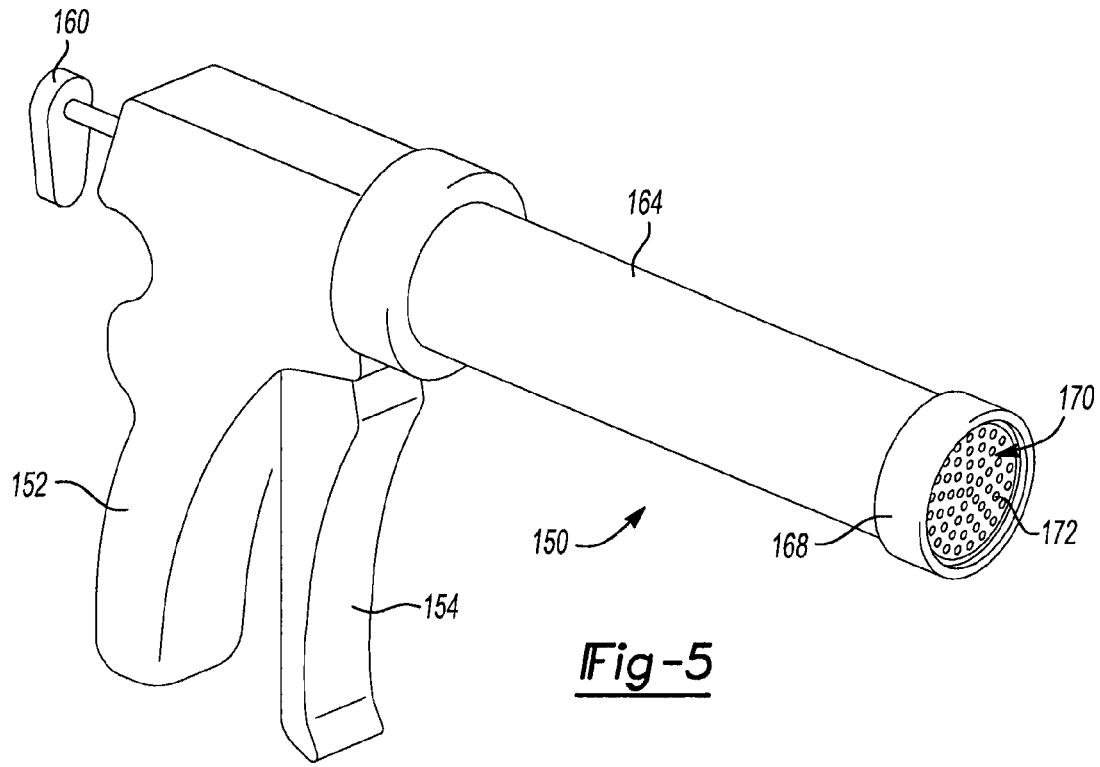
FIG. 5 is a perspective view of a tissue disrupter, according to various embodiments.
Figure 6:
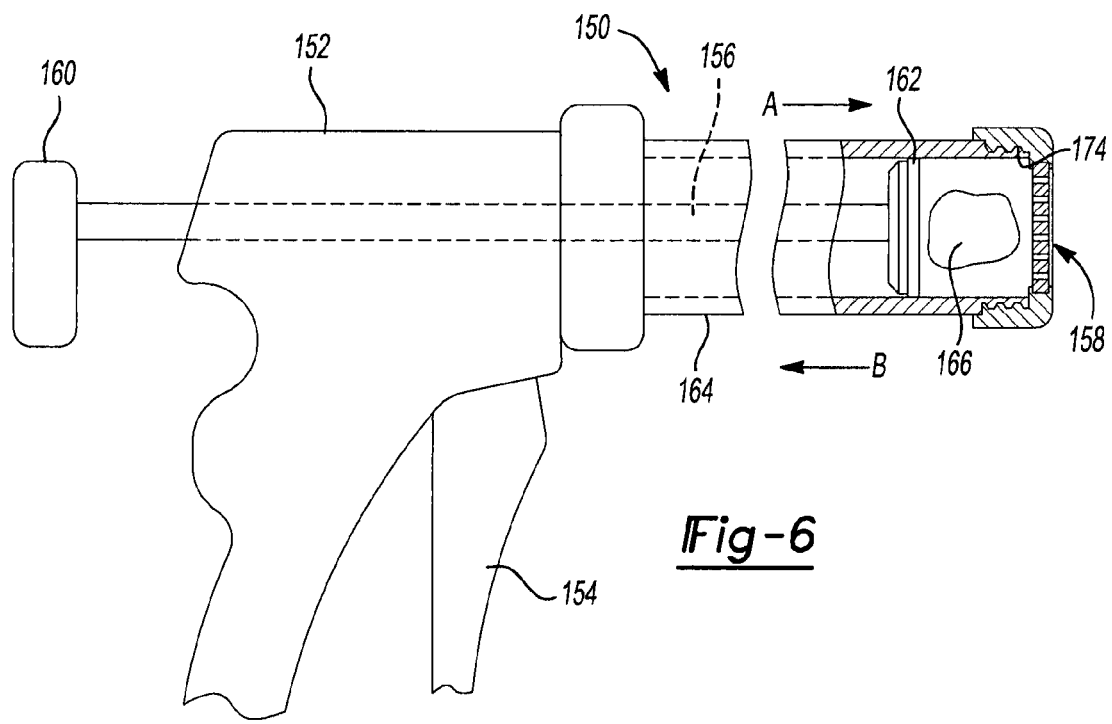
FIG. 6 is a plan view of a tissue disrupter, according to various embodiments.

According to various embodiments, a disruption assembly 150 is illustrated in FIGS. 5 and 6. The disruption assembly 150 can include a single pass, non-reciprocating bone cement gun configuration. Various such bone cement gun assemblies include the Optigun™ assembly sold by Biomet, Inc. of Warsaw, Ind., USA as a part of the Optivac™ Cement Mixing System. Briefly, the bone cement gun assembly 150 can include a main handle portion 152 and a power actuating handle 154. Generally, the power handle 154 can move relative to the main handle 152 to cause a movement of an actuating rod 156. The connection of the handles 152, 154 and the rod 156 can be any appropriate connection. For example, a pawl and ratchet system can be used to advance the rod 156 in a selected direction, such as the direction of arrow A towards an exit end of 158 of the assembly 140. A release mechanism can be depressed or moved to allow withdrawal or movement of the rod 156 in a direction of an arrow B towards the handle assembly 152. Movement of the rod 156 towards the handle assembly can be performed via manual movement or automatic movement, such as pulling on a retraction handle 160.

The rod 156 can terminate in a plunger 162 held within a canister or tube 164. Near the exit end 158 of the tube 164 can be a frit or disruption assembly 168. A sample of tissue 166, such as adipose tissue, can be introduced into the tube 164 for purposes of disruption. The sample of tissue can be introduced into the tube 164 in various manners. For example, the frit assembly 168 can be removed or the entire tube 164 can be removed from the trigger body. In this way, a sample can be introduced into the tube 164 for disruption or extrusion through the frit assembly 168.

The frit assembly 168 can include a frit body 170 that defines one or more passages or holes 172. The passages 172 can include any appropriate dimension, such as those discussed above. As the assembly 150 is actuated, the plunger 162 can move the adipose tissue sample 166 through the holes 172 defined in the frit assembly 168. This can cause a mechanical disruption of the sample 166 as it passes through the frit assembly 168.

As discussed above, the frit assembly 168 can include any appropriate frit or hole dimensions. Also, the holes, according various embodiments, can be provided in any appropriate shape or configuration. Further, the frit assembly 168 can be removeable, such as via a threaded interconnection with threads 174 so that the frit assembly 168 can be applied or removed from the tube 164. This can allow for introduction of the sample into the tube 164 or exchange of the frit assemblies 168. For example, a kit can include a plurality of the frit assemblies 168, each including different dimensions of the throughbores 172. The tissue sample 166 can be pressed through a first frit assembly 168, the first frit assembly can then be removed, the sample replaced in the tube 164, a different frit assembly positioned on the tube 164, and the sample again pressed through the new frit assembly. Therefore, the tissue sample can be progressively and increasingly disrupted as it moves through a plurality of the frit assemblies.

Figure 7:
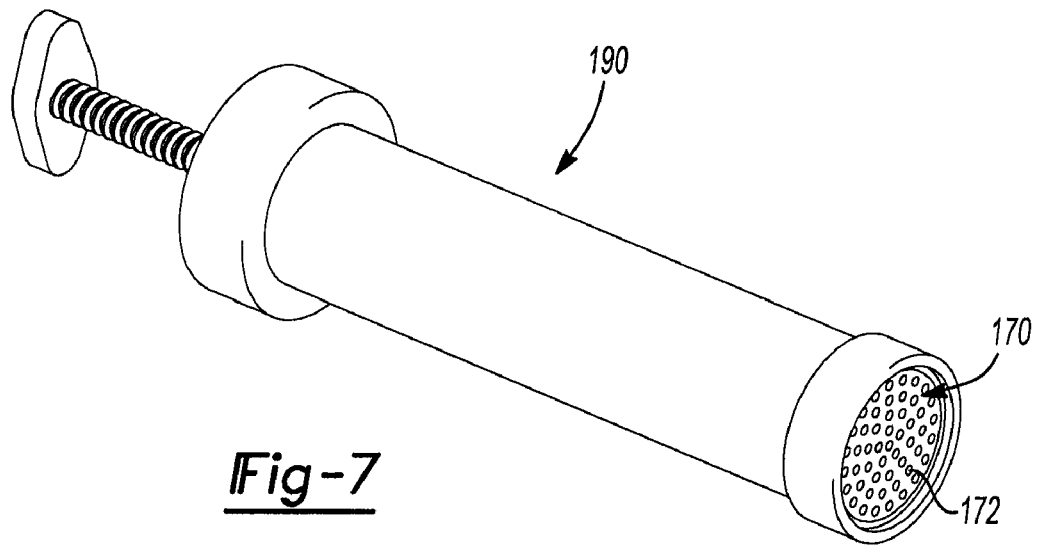
FIG. 7 is a tissue disrupter, according to various embodiments.
Figure 8:
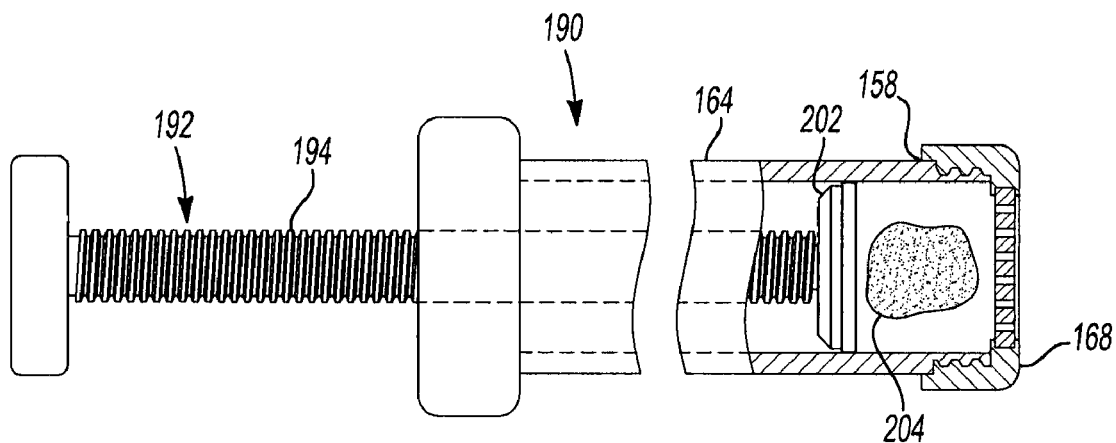
FIG. 8 is a plan view of the tissue disrupter of FIG. 7.
Figure 9:
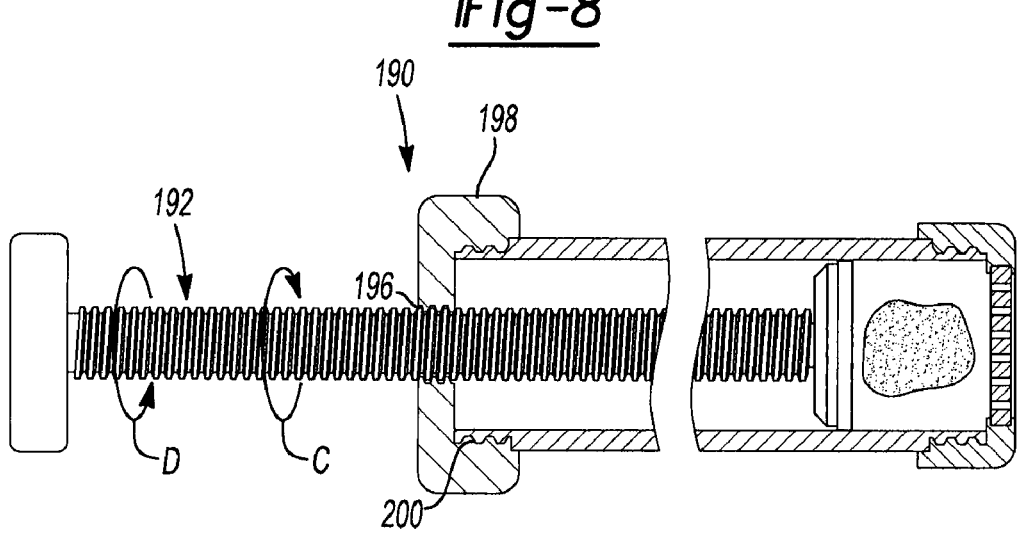
FIG. 9 is a plan transparent view of the tissue disrupter of FIG. 7.

With references to FIGS. 7-9, a disruption assembly 190 is illustrated. The disruption assembly 190 can include portions that are similar to the disruption assembly 150 and similar reference numerals are used to identify these portions and discussed again only briefly. For example, the disruption assembly 190 can include a tube 164 that has a terminal or exit end 158 and a frit assembly 168 positioned near the terminal or exit end 158. The frit assembly 168 can include a frit body 170 that defines one or more throughbores or holes 172. As discussed above, an aspiration needle could be considered one very long hole.

The disruption assembly 190 can include a rod 192 that defines an external thread 194. The external thread can engage an internal thread 196 defined in an end cap or end portion 198 of the disruption assembly 190. The end cap 198 can be removeable from the tube 164 via a threaded engagement 200. The rod 192, however, can be rotated in an appropriate direction, such as the direction of arrow C to advance the rod towards the exit end 158 that, in turn, can push a plunger 202 towards the exit end 158. A sample 204, such as an adipose tissue sample, can be pressed through the holes 172 defined by the frit body 170 in the frit assembly 168. The rod 192 can also be rotated in a counter direction, such as generally in the direction of arrow D, to move the plunger 202 towards the end cap 198. This can allow the plunger 202 to be moved back and forth within the tube 164 and can allow for filling of the tube 164, such as with removal of the frit assembly 168. Further, as discussed in relation to the disruption assembly 150, a kit can include a plurality of the frit assemblies 168 each including holes 172 of different sizes. Therefore, the sample 204 can be pushed through a frit assembly including a first hole size and reloaded into the tube 164 and pushed through a second frit assembly including a second hole size.

Regardless of the configuration of the disruption assembly, it can be selected to disrupt a tissue sample to a selected particle or cluster size. For example, the cluster sizes can be selected to be any appropriate dimension, such as those discussed above. Further, as discussed in relation to the various disruption assemblies, one or more passes through one or more frit assemblies may be selected to achieve an appropriate particle size. Therefore, it will be understood that a disruption can include one or more passes through a frit assembly and various procedures, such as quality control procedures, can be used to ensure that an appropriate particle size is achieved. Therefore, the disruption assemblies, according to various embodiments, can be provided alone or in combination with other disruption assemblies to achieve an appropriate particle size, such as those discussed above.

Regardless of the disruption assembly provided, once disruption occurs the disrupted sample can be further separated or purified to acquire a selected component, such as a selected cell population. For example, a pluripotent or stem cell population can be extracted from the tissue sample (e.g. disrupted adipose tissue). Various techniques can be used to separate the pluripotent or stem cells from the disrupted tissue including those discussed further herein.

Figure 10:
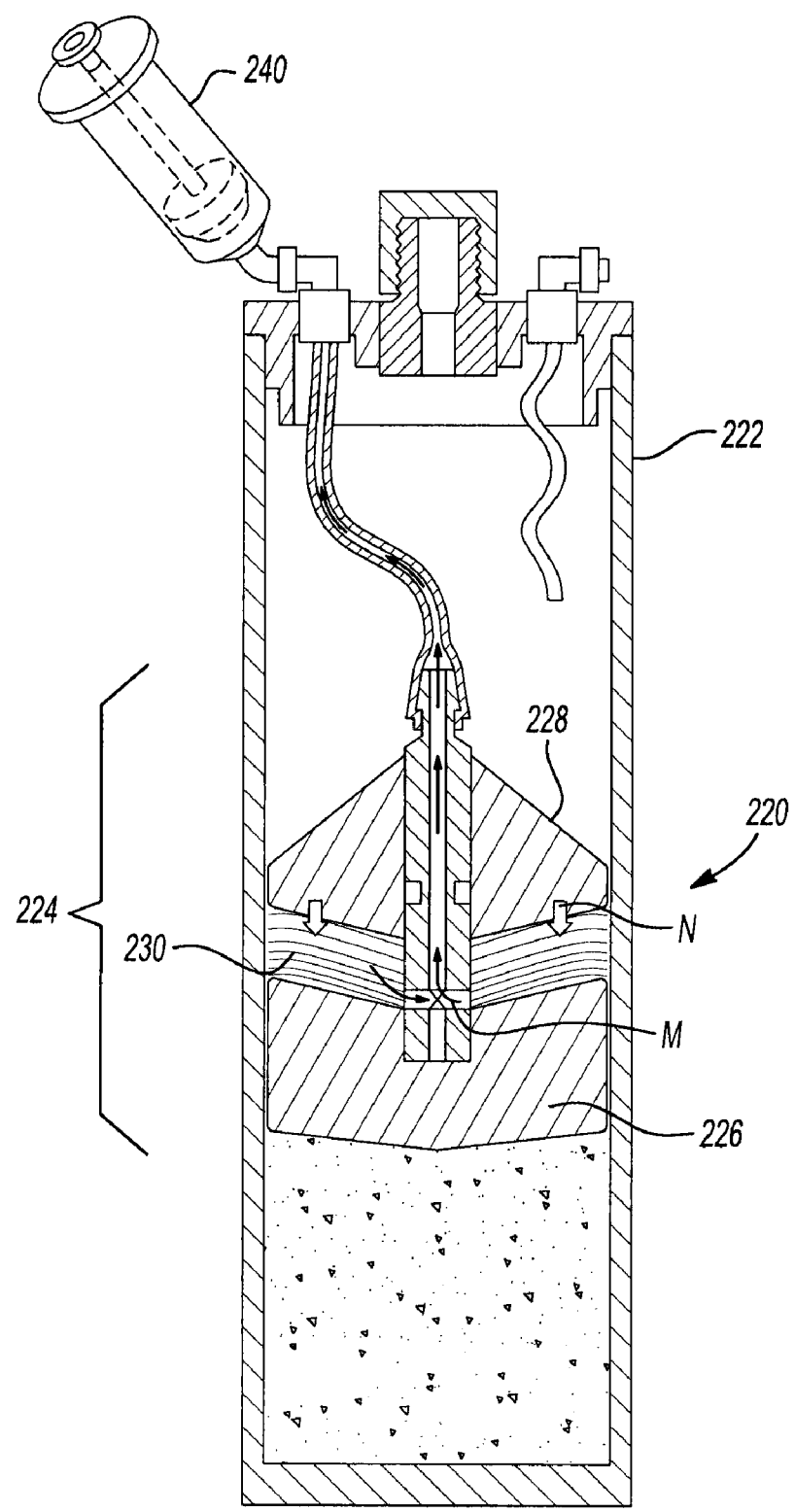
FIG. 10 is a cross-sectional view of a tissue isolator, according to various embodiments.

With reference to FIG. 10, a tube or separation assembly 220 can be used. A separation assembly 220 can include a tube 222 and a separation buoy system 224. The buoy system 224 can include a first buoy member 226 and a second buoy member or isolator portion 228. The first and second buoy portions 226, 228 can be fixed relative to one another or moveable relative to one another. Further, either or both of the buoy assembly portions 226, 228 can be tuned to a selected density or specific gravity to allow for a collection area 230, defined between the two buoy portions 226, 228, to be provided at an equilibrium position that can include the selected cell population, such as the pluripotent cells from an adipose tissue sample. A syringe 240, or other appropriate collection or extraction device can be used to collect the material from within the tube 222. Appropriate separation tubes can include the GPS II™ separation system sold by Biomet, Inc. of Warsaw, Ind., USA.

Figure 11:
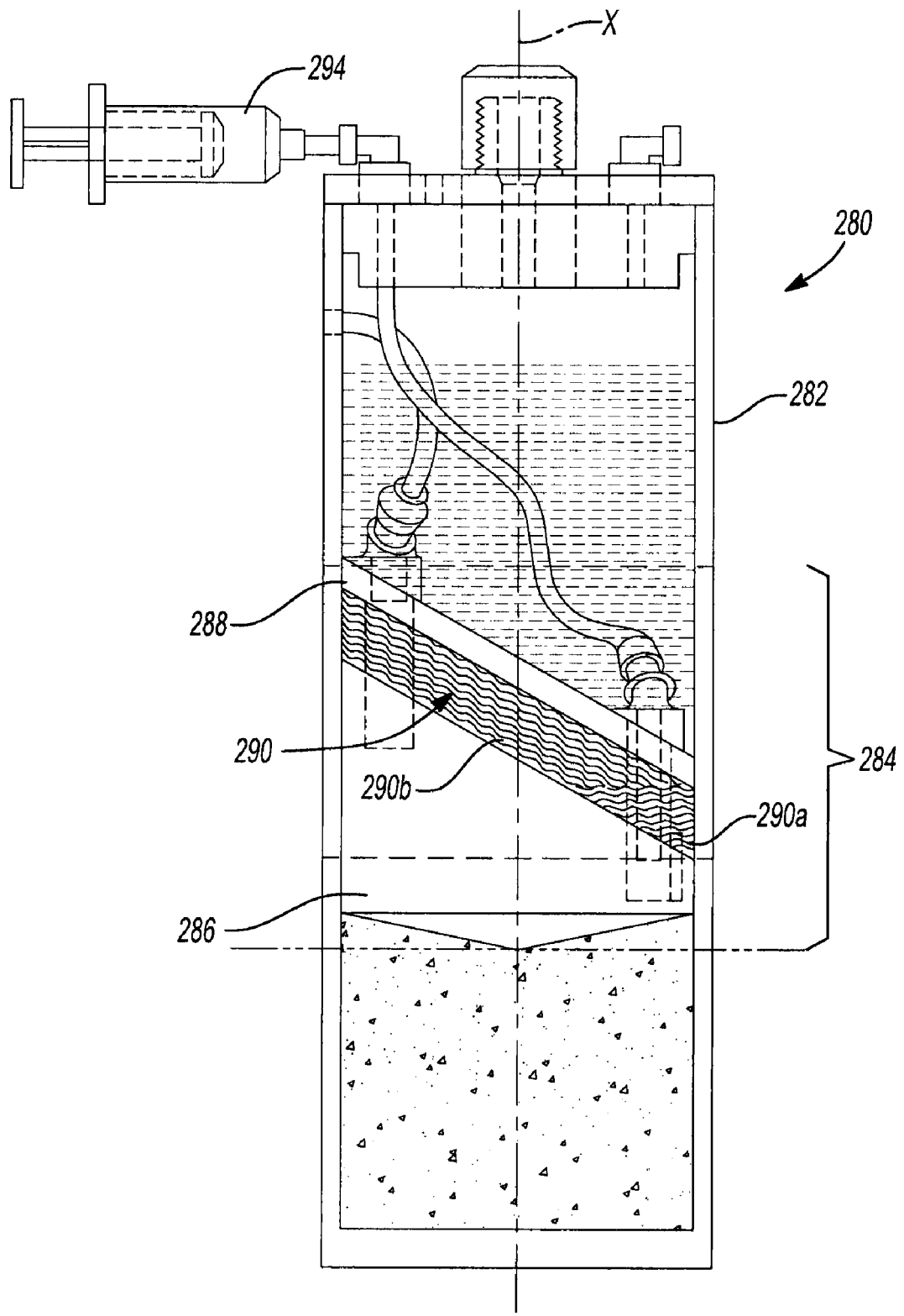
FIG. 11 is a plan view of a tissue isolator, according to various embodiments.

With reference to FIG. 11, according to various embodiments, a separation tube assembly 280 is illustrated. The separation tube assembly 280 can include a separation tube 282 that includes a separation buoy assembly 284. The buoy assembly 284 can include a main buoy portion or buoy 286 and a second buoy portion or isolator 288. The isolator 288 can be separated from the buoy portion 286 by a distance to define a collection area 290. Within the collection area 290, two or more collected materials or material areas 290a, 290b can be formed.

Again, the assembly of the buoy portion 286 and the isolator 288, or selected portions thereof, can include a tuned density or specific gravity to position the collection area 290 at a selected equilibrium position of a sample that is positioned within the tube 282. Also, an appropriate collection or extraction syringe or device 294 can be used to collect material from the tube 282. Selected separation tubes can include the GPS III ™ system sold by Biomet, Inc. of Warsaw, Ind., USA. Further exemplary buoy separation systems are disclosed in U.S. patent application Ser. No. 12/101,594, filed on Apr. 11, 2008, now U.S. Pat. No. 7,992,725, incorporated herein by reference.

It will be understood, however, that appropriate separation tubes can be designed in appropriate manners to allow for separation of a selected population from the tissue sample. Further, the separation tubes, such as the separation tubes 220, 280 can be provided with separation or power systems, such as a centrifuge system. The centrifuge system can provide a separation force or gravitational force to the sample and the buoy positioned within the tubes to allow for separation of the sample position within the tubes.

Figure 12:
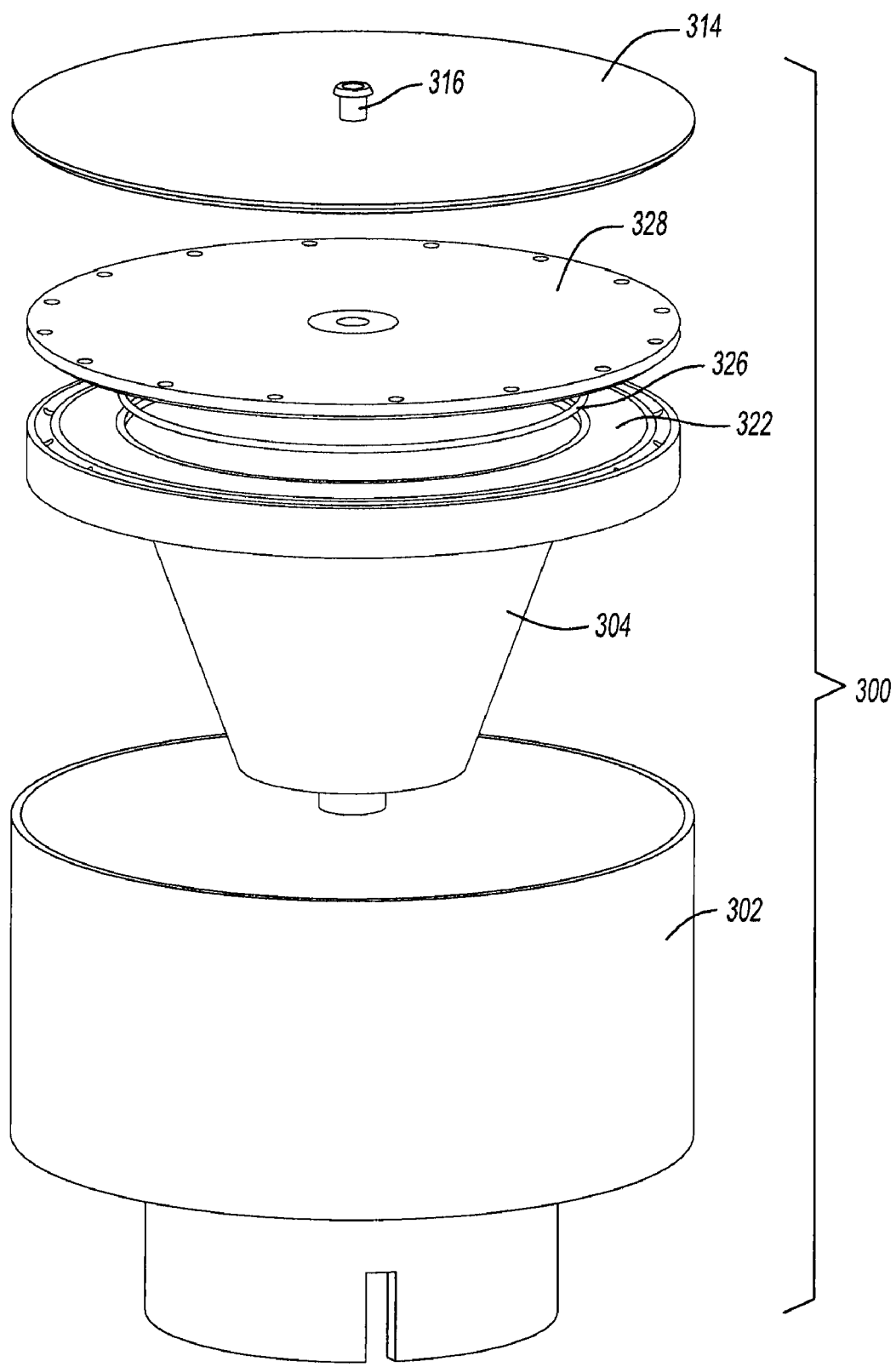
FIG. 12 is a plan perspective exploded view of a tissue isolator, according to various embodiments.
Figure 13:
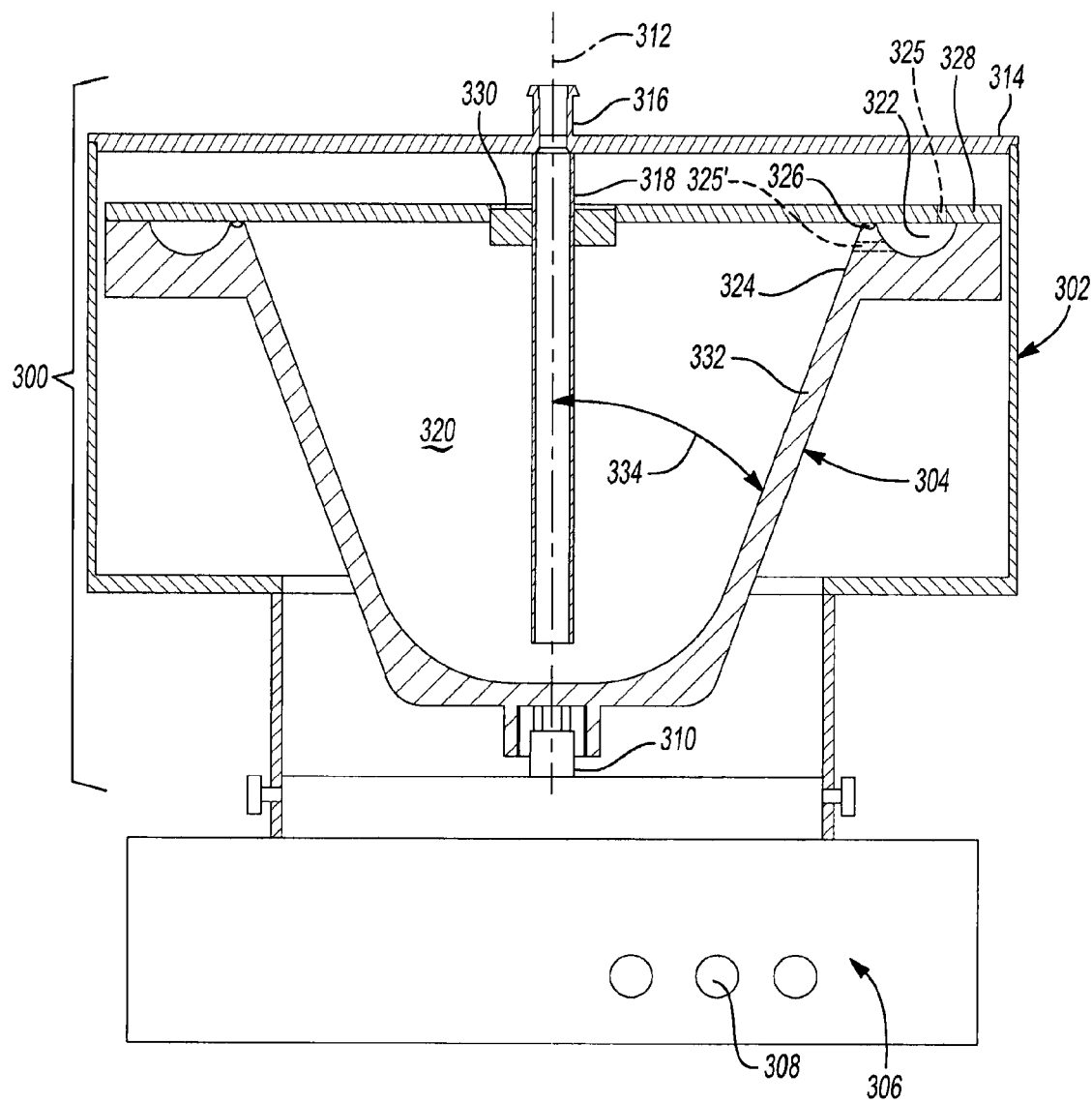
FIG. 13 is a cross-sectional view the tissue isolator of FIG. 12.

With reference to FIGS. 12 and 13, a separation system 300 is illustrated. The separation system 300 can include three main components. The three main components can include an outer chamber or housing 302, an inner chamber or container 304, and a drive base 306. The drive base 306 can include controls 308 and an internal motor or power source to drive a rod or axle 310. The outer housing 302 can surround all or part of the drive base 308 and the axle 310. The motor base 306 can spin the inner container 304 around a central axis 312 defined by the axle 310 and a portion of the inner chamber 304. As discussed further herein, rotation around the axis 312 can cause a force within the chamber 304 to create a separation of material positioned within the chamber 304.

The outer housing 302 can engage or include a lid 314 that includes a connection or port 316. The port 316 can interconnect with a conduit or cannula 318 to allow for introduction or extraction of a material from a main container area 320 of the inner chamber 304. The main container area 320 can be used to hold a material before and during a portion of the separation in an isolation process, as discussed further herein. Further, the lid 314 may include additional ports for access to other areas of the housing 302 or the container 304, such as an isolation area, including an annular isolation ring 322.

The inner container 304 can include the main container area 320 and the isolation area 322 separated by a wall portion 324, a sealing member, such as an o-ring 326, and a lid 328. The lid 328 can be held relative to the wall portion 324 and the sealing member 326 in any appropriate manner, such as by gravity or a biasing mechanism. The lid 328 can be allowed to move relative to the central cannula 318 according to any appropriate method, such as via a bearing 330. The lid 328 can move relative to the o-ring 326 at a selected time, as discussed further herein, to allow for an opening between the main chamber area 320 and the isolation area 322. The movement of the lid 328 can be along the axis 312 or can include a movement of a portion of the lid 328 to allow for an opening between the main chamber 320 and the isolation area 322.

An optional vent 325, 325' for the isolation area 322 on the side of a barrier wall 344 (FIG. 14A) opposite an extraction port 346 (FIG. 14A) can be provided, according to various embodiments. The vent 325 can optionally open to the space above the flexible lid or liner. Alternatively, the vent 325' can optionally open to the central chamber 320. The vent 325, 325' can allow air to enter the isolation area 322 to replace the volume of material withdrawn and for air to alternately escape if the material is jetted in and out to improve cell re-suspension and recovery during material collection, such as cellular material. The vent 325, 325' can also be used as a port for introduction of a stream of wash solution. The vent 325, 325' can also include a two-way or one-way valve that is manually or automatically operated based upon pressure differentials or other mechanism.

The main chamber area 320 can include any appropriate volume or dimension. For example, a wall 332 of the main chamber area can define an angle 334 between the central axis 312 and the wall 332. The angle can be any appropriate angle, such as between about zero degrees and about ninety degrees, but generally less than ninety degrees. The angle 334 can also include about one degree to about forty degrees, and further include about ten degrees to about thirty degrees, and may also include about twenty degrees. The angle 334 can be provided or selected to assist in a separation or movement of material from the main chamber area 320 to the isolation area 322.

In addition, the inner chamber 304 can be formed of any appropriate materials, such as a material that includes a selected co-efficient of friction relative to the material positioned within the inner chamber 304 for separation. For example, an adipose tissue sample can be positioned within the inner chamber 304, such as within the inner area 320, for separation. It can be selected to include a co-efficient of friction between the adipose sample or a portion of the adipose sample to achieve a selected separation at a selected period of time and/or under a selected force, such as a centrifugal force.

Figure 14A:
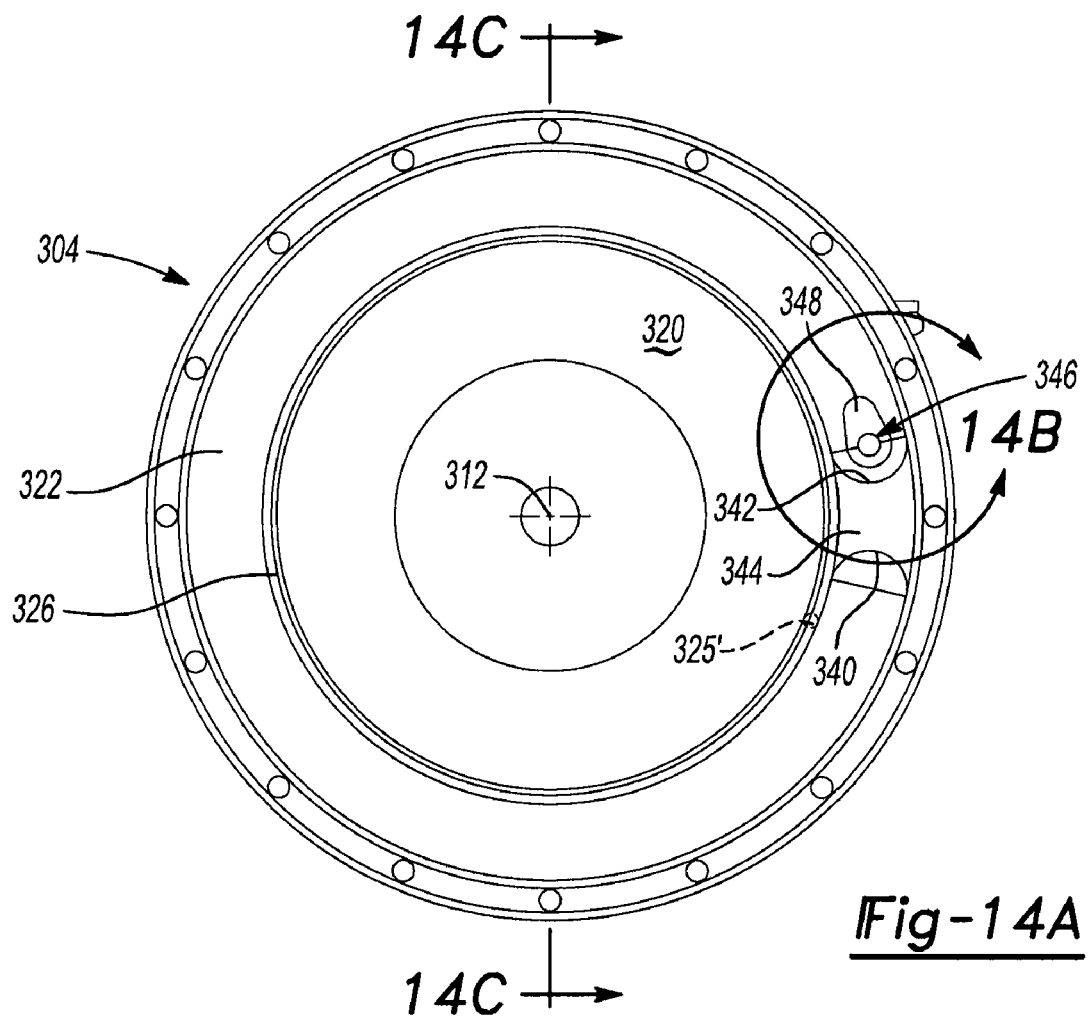
FIGS. 14A-14C are various detailed views of the tissue isolator of FIG. 12.
Figure 14B:
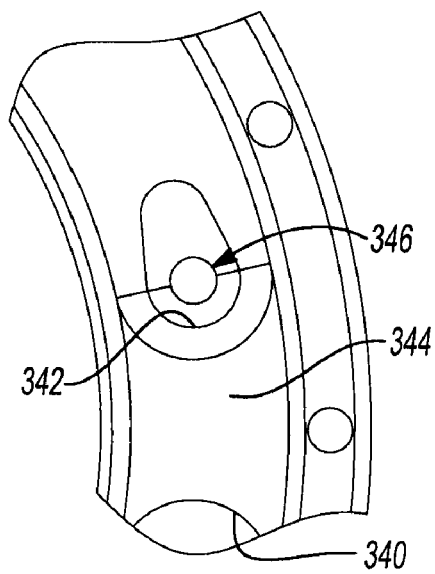
Figure 14C:
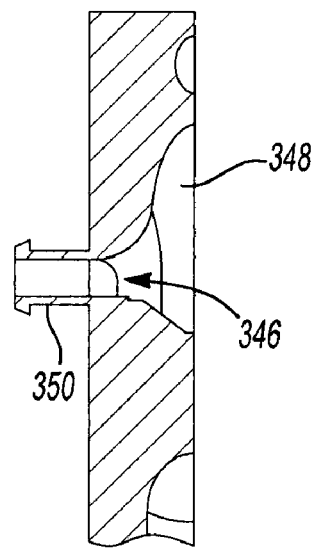

With further reference to FIGS. 14A-C, the inner chamber 304 is further illustrated. The inner chamber 304 can include the isolation area 322 separated from the main containment area 320. The isolation area 322 can include a complete or a partial annular ring surrounding the inner chamber or area 320. In addition, multiple isolation areas 322 can be provided, for example as multiple concentric annular rings (not specifically illustrated). The multiple isolation areas 322 could be used to isolate multiple fractions of intermediate or multiple densities (e.g., buffy coat from whole blood). A sealing portion or valve can be provided between each or any appropriate group of the multiple isolation areas. For example, the lid 328 or liner can include multiple regions to act as sealing portions between each of the concentric isolation areas. In this way, multiple specific and discrete materials can be separated and/or concentrated.

When a partial annular ring is provided, the isolation area 322 can extend from a first end 340 to a second end 342 that can be less than 360 degrees around the central axis 312 from the first end 340. As discussed further herein, the inclusion of the first end 340 and the second end 342 separated by a wall or barrier portion 344 can allow for substantially complete extraction of a material from the isolation area 322. Briefly, if the wall 344 were not present it may be difficult to extract material from an area not adjacent to an extraction port, such as the extraction port 346. The extraction port 346 can be positioned near or within a well or sump 348 that can further assist in removing material from the isolation area 322. The inclusion of the wall 344 allows for a vacuum to be created within the isolation area 322 relative to the extraction port 346 and allow for further extraction or efficiency of extraction from the isolation area 322.

The extraction port 346 can be accessed from any appropriate location. Examples include, through the lid 328 of the inner container 304, the lid of the exterior chamber 314, or any other area through the housing 302 or relative to the housing 302. Further, the extraction port 346 can include a cannula or connection portion 350 that extends from the port 346 and can be interconnected with any appropriate portion, such as a tube, extraction syringe, or any other appropriate mechanism. Material from the isolation area 322 can be extracted for various purposes, including those discussed further herein.

Figure 15:
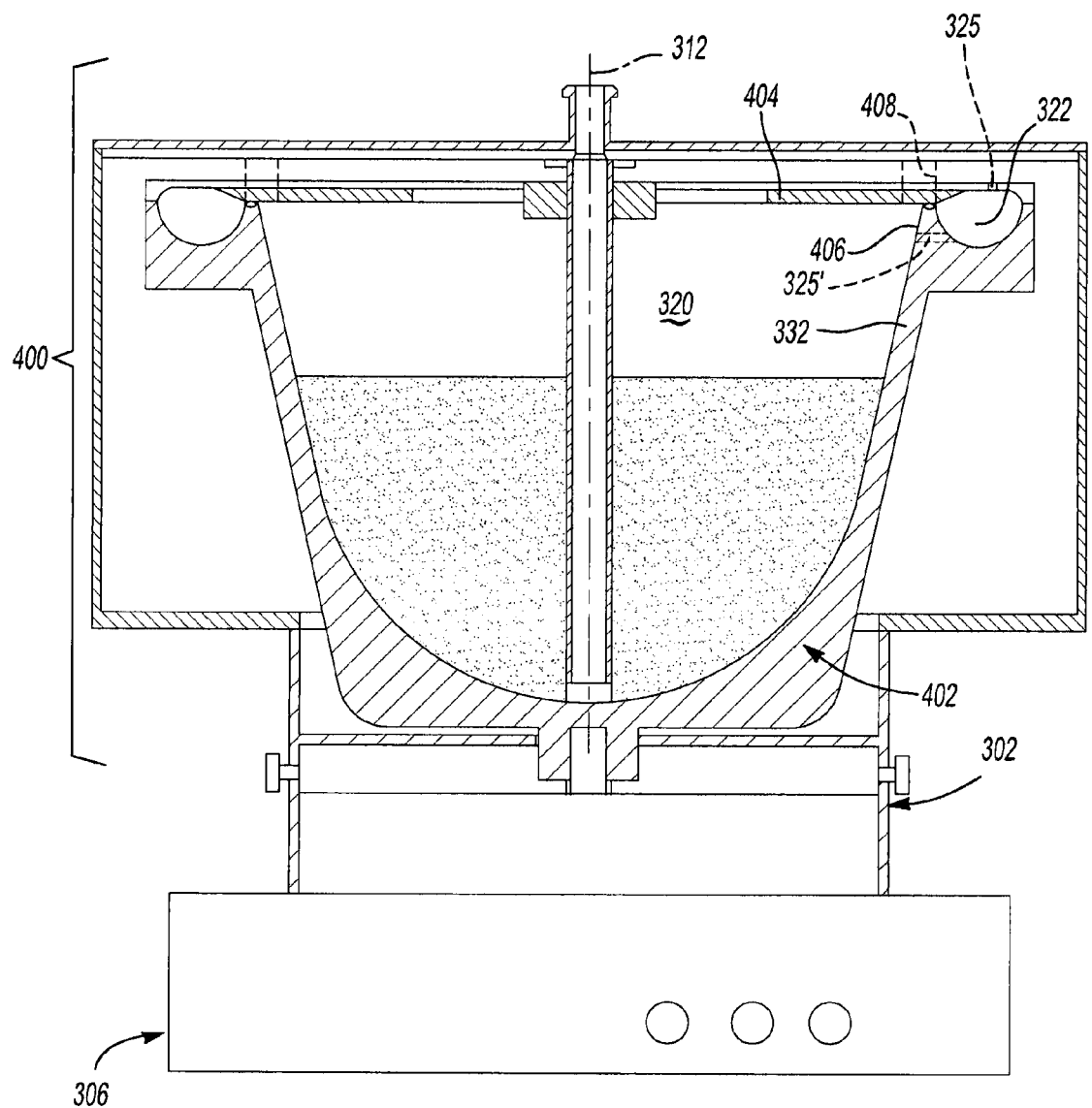
FIG. 15 is a tissue isolator, according to various embodiments.
Figure 16A:
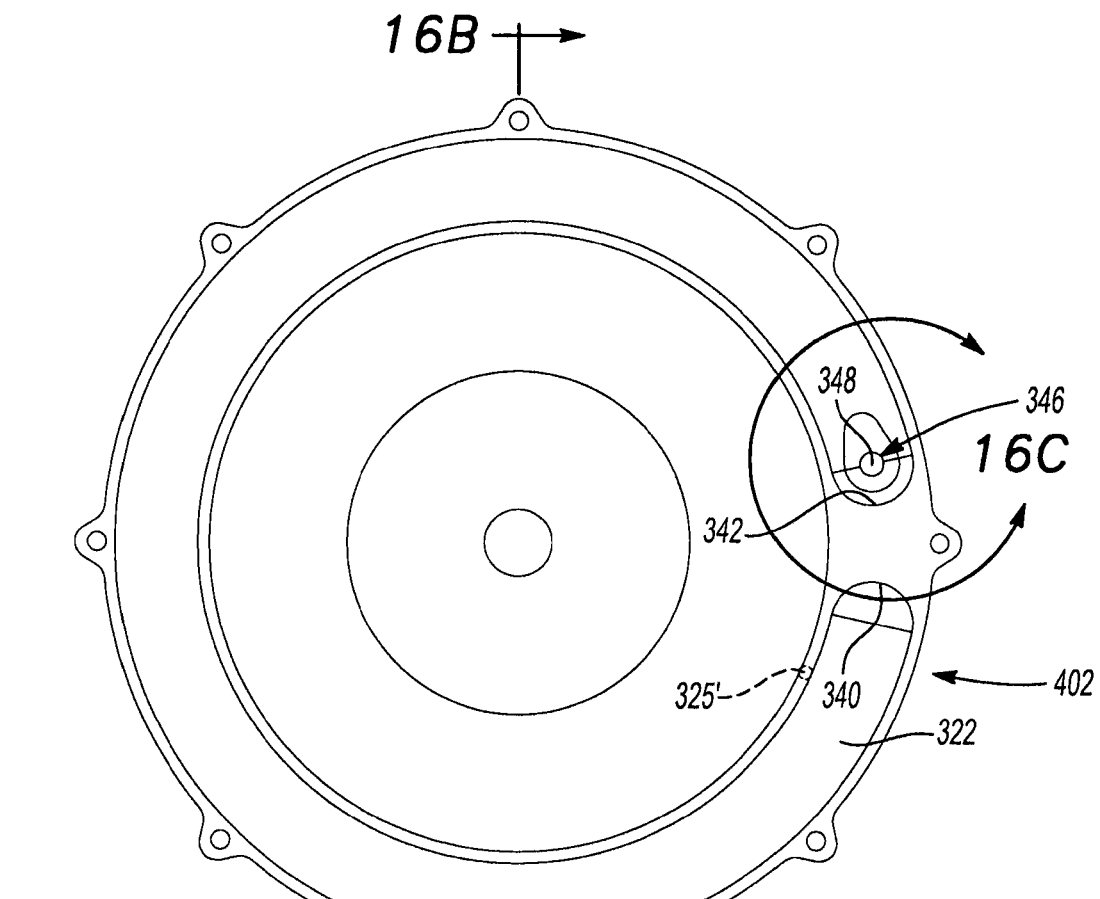
FIG. 16A-16D are various detailed views of the tissue isolator of FIG. 15.
Figure 16B:
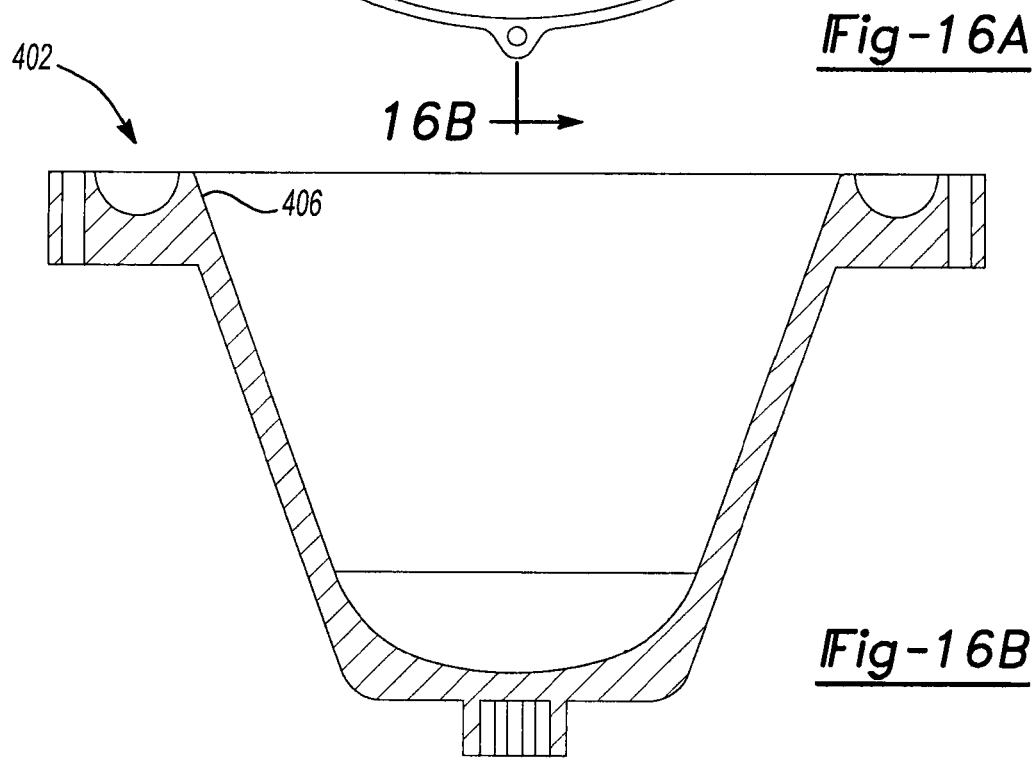
Figure 16C:
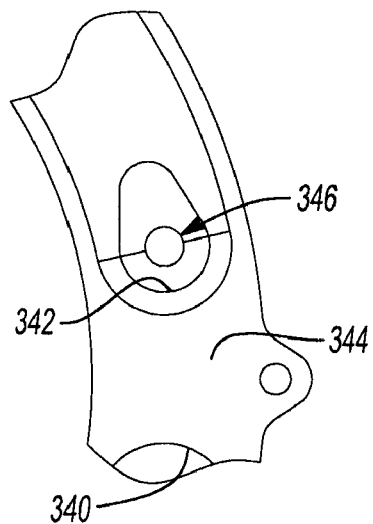
Figure 16D:
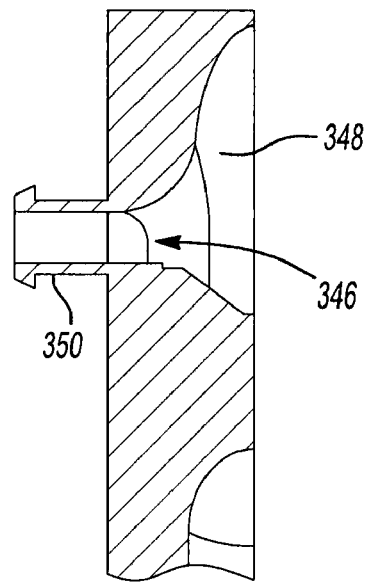

With reference to FIGS. 15 and 16 A-D, a separation assembly 400 is illustrated. The separation assembly 400 can be substantially identical to the separation assembly 300 except for various specifics of an inner chamber 402. Therefore, the outer housing 302 and the drive base 306 are simply illustrated and will not be discussed in detail here. The inner chamber 402 can also be substantially similar to the inner chamber 304. For example, the inner chamber 402 can include the central axis 312, the isolation area 322, the optional vents 325, 325', and the main inner chamber 320. Further, the various portions such as the wall 332 can be formed of similar materials and positioned at respective locations and orientations relative to other portions of the chamber 402.

The inner chamber 402, however, can differ from the inner chamber 304, illustrated in FIG. 13, at least by a lid 404 positioned relative to a wall portion 406 of the inner chamber 402. The lid portion 404 can be formed of a substantially flexible material, or a least an external or periphery portion 408 can be formed of a flexible portion. Further, the inner chamber 402 can be provided to not include the sealing member 326 provided with the inner chamber 304. The flexible portion 406 of the lid 404 can flex relative to the isolation area 322 at a selected time, as discussed further herein. Further, the flexible portion 408 of the lid 404 can also form a seal relative to the portion 324 of a wall 406. Therefore, rather than having the lid 328 that can move relative to the sealing member 326, the lid 404 can define a flexible portion 408 that can act as a sealing portion relative to the upper wall portion 406 and also flex relative to the upper wall 406. When the flexible portion 408 flexes it can provide an opening over the wall 406, thus it can act as a valve.

The lid 404 can be designed to flex at a specific location or at a specific region. It will be understood, however, that this is not necessary. The lid 404 can be provided to generally flex an appropriate amount. For example, the lid may flex at a periphery or near a center of the lid. The lid 404 can be formed of appropriate materials and of appropriate dimensions to allow the appropriate amount of flexing.

The lid 404 may also be provided as a liner over which an additional lid is provided. The additional lid or outer cover lid can provide a stop or limit to the amount of flexing or movement of the lid liner 404, under the outer lid. Accordingly, it will be understood that the lid 404 or any other appropriate flexible member and can be provided to allow an escape of a selected cell fraction into the isolation area.

The inner chamber portion 402 can also define the withdrawal port 346, the sump 348, and the withdrawal cannula 350. The isolation area 322 can further include the two ends 340, 342 separated by the barrier area 344. Accordingly, the inner chamber 402 can operate substantially similar to the inner chamber 304, as discussed further herein, but can include the flexible portion 408 of the lid 404 rather than a separate and distinct sealing member, such as the sealing member 326.

Figure 17:
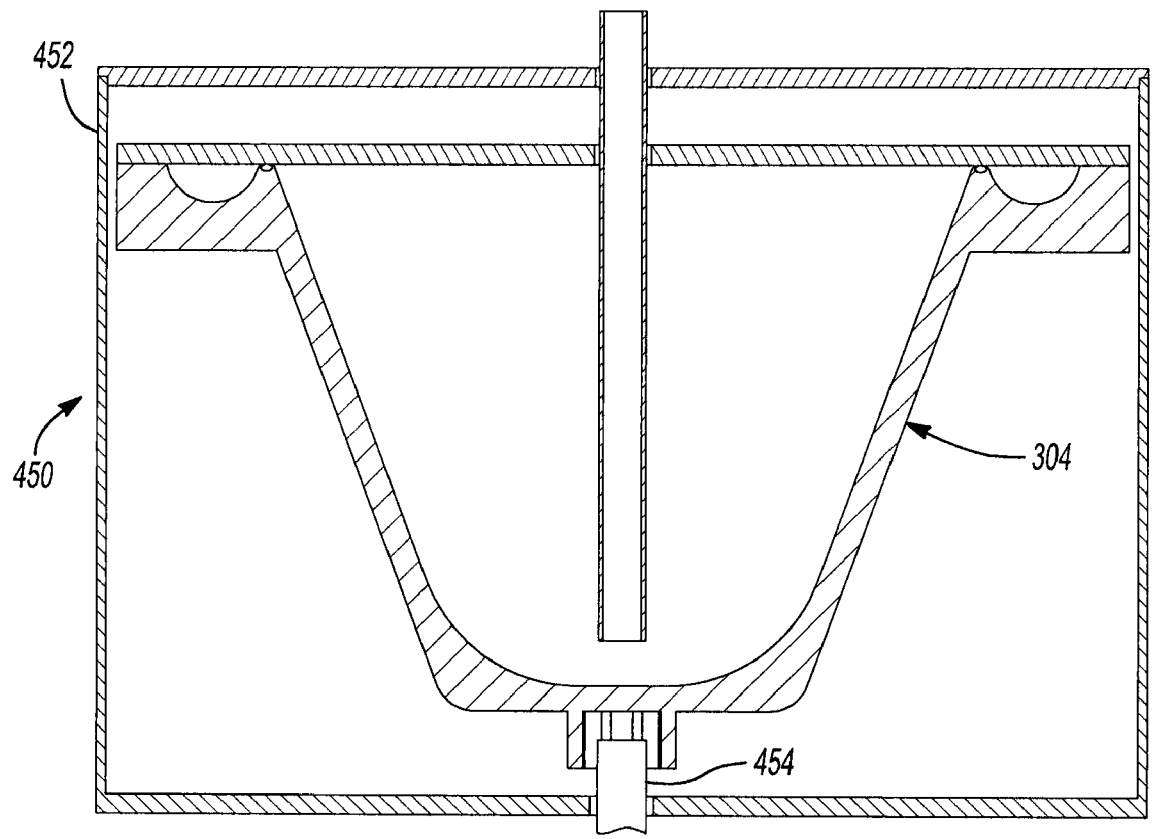
FIG. 17 is a cross-sectional view of a tissue isolator, according to various embodiments.

With reference to FIG. 17, a separation assembly 450 is illustrated. The separation assembly 450 can include an outer housing 452 that can generally include a standard centrifuge system, such as the tissue centrifuge system sold by Drucker or the CentraCL3 sold by Thermo Scientific. The centrifuge system can include a selected drive system or motor that can drive an axle or rod 454. The drive portion of the separation system 450, however, can be substantially or relatively more powerful than the drive system 306. Further, the outer housing 452 can be more robust or heavier and allow for reduced vibrations during separation and rotation of the separation inner chamber 304, or any appropriate inner chamber. The inner chamber 304 can be substantially similar to the inner chamber 402 discussed above except that it can be rotated by any appropriate motor or drive system. Therefore, the separation chamber 304 can be driven at any appropriate separation or drive speeds or for any appropriate length of time to allow for separation of a selected material.

With reference to FIGS. 18A-18G, the separation system 300 can be used to separate a selected component from a sample, such as in block 32 of FIG. 1. It will be understood that the separation system 300, however, can include various portions, either alone or in combination, such as the sealing member 326 or the flexible portion 408. Therefore, although the separation system 300 is illustrated in FIGS. 18A-18G, any appropriate separation system can be used and this is merely exemplary. Also, although the following discussion exemplary discusses separation of adipose tissue, any appropriate tissue can be separated. In addition, any appropriate cell fraction can be separated from the tissue sample.

As discussed above, a sample, such as an adipose tissue sample, can be agitated or disrupted according to various embodiments, including those discussed above. Once the tissue sample is appropriately disrupted, it can be mixed with various materials. Materials that can be mixed with the sample include citrate, a biologically acceptable acid, EDTA, or other appropriate materials. It will be further understood that a material or solution can be added at any appropriate time, such as prior to disruption of the sample, for pH adjustment, chelating, lysing, etc. It can be selected to create a solution 480 that can be placed within the main container area 320 of the inner chamber 304. The solution 480 can include the sample, such as the adipose sample, and any appropriate materials, such as citrate. The solution 480 can be adjusted to any appropriate pH and can include chelating agents, such as citrate or EDTA. Regardless it can be selected to include with the tissue sample various extra cellular materials, such as extra cellular matrix.

Various materials, however, need not be provided. For example, no extrinsic enzymes or extrinsic collagenase need be added to the solution 480. The disruption and the separation system can provide an appropriate separation of the tissue sample. This can also provide a final product that lacks extrinsic enzymes which can eliminate the need to attempt to remove selected enzymes. The absence of extrinsic enzymes can also eliminate concern of contamination or patient rejection. Although naturally occurring enzymes may be present in the tissue sample, which are not specifically removed, extrinsic enzymes are those added to the tissue sample whether artificially formed or not.

The sample can be placed into the inner chamber 304 in any appropriate manner, such as through the entry port 316 from a supply vessel 482. The supply vessel 482 can include the syringes, as discussed above, or any appropriate supply vessel. Further, as discussed above, the tissue sample can be provided from a patient to whom the selected material will be supplied. In various embodiments, the selected cell population can be substantially autologous. Once the solution 480 is positioned within the inner chamber 304, the drive base 306 can be activated to drive the inner chamber 304 in a selected manner, such as in a rotation around the central axis 312.

Figure 18A:
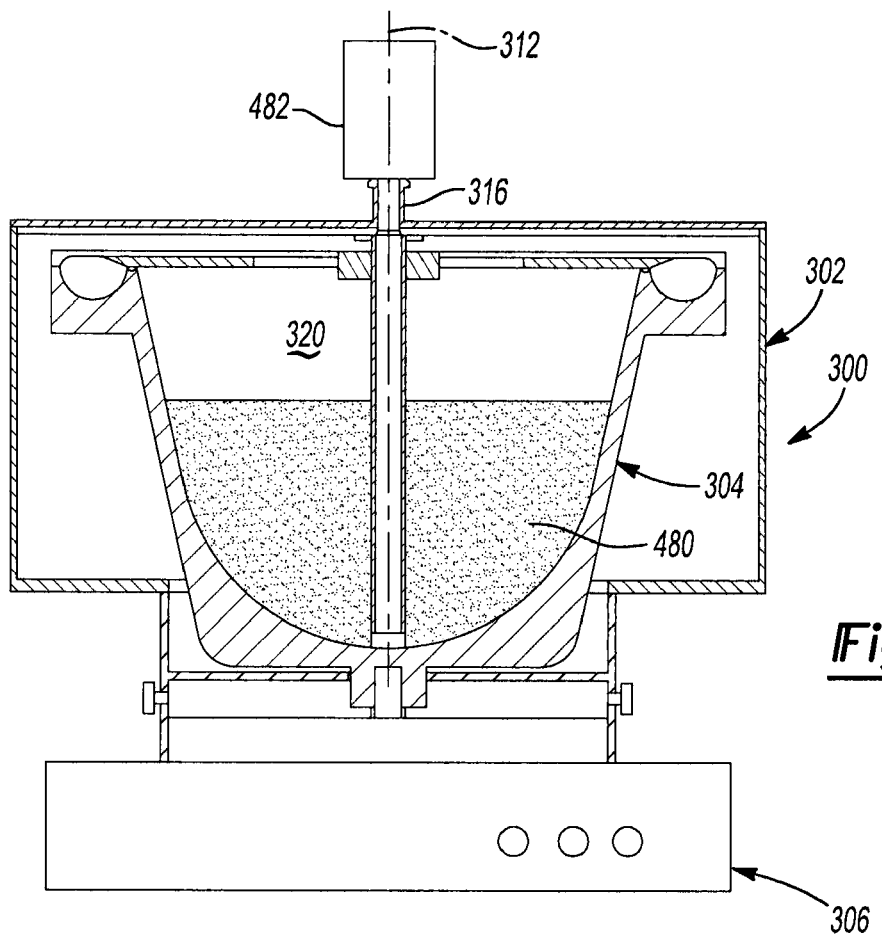
FIGS. 18A-18G illustrate a separation procedure of a tissue sample, according to various embodiments.
Figure 18B:
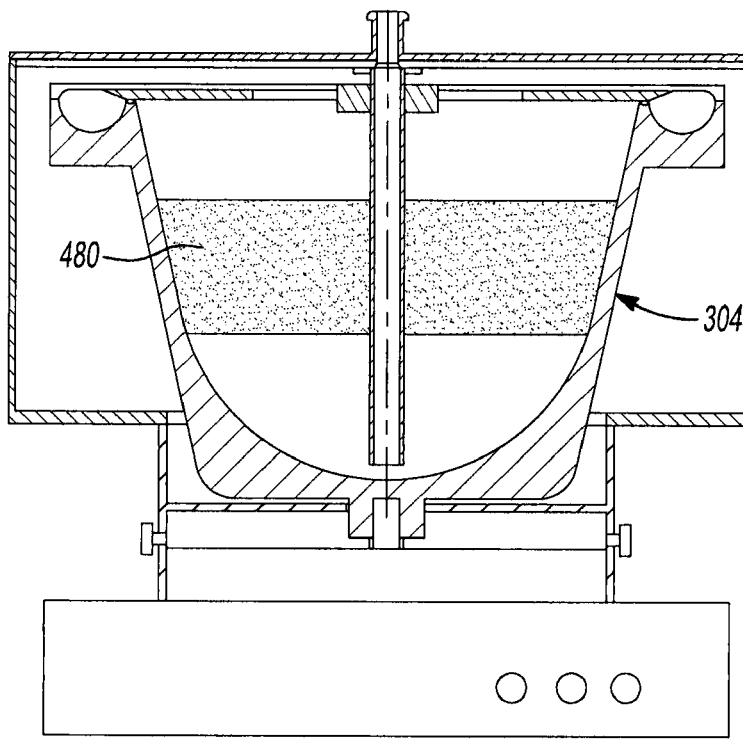
Figure 18C:
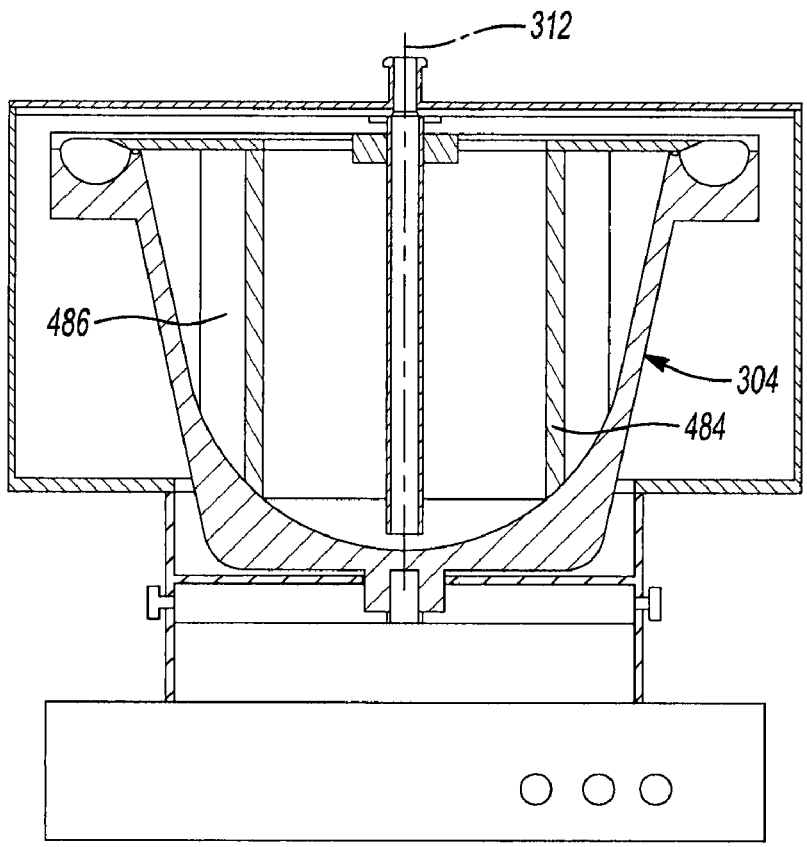
Figure 18D:
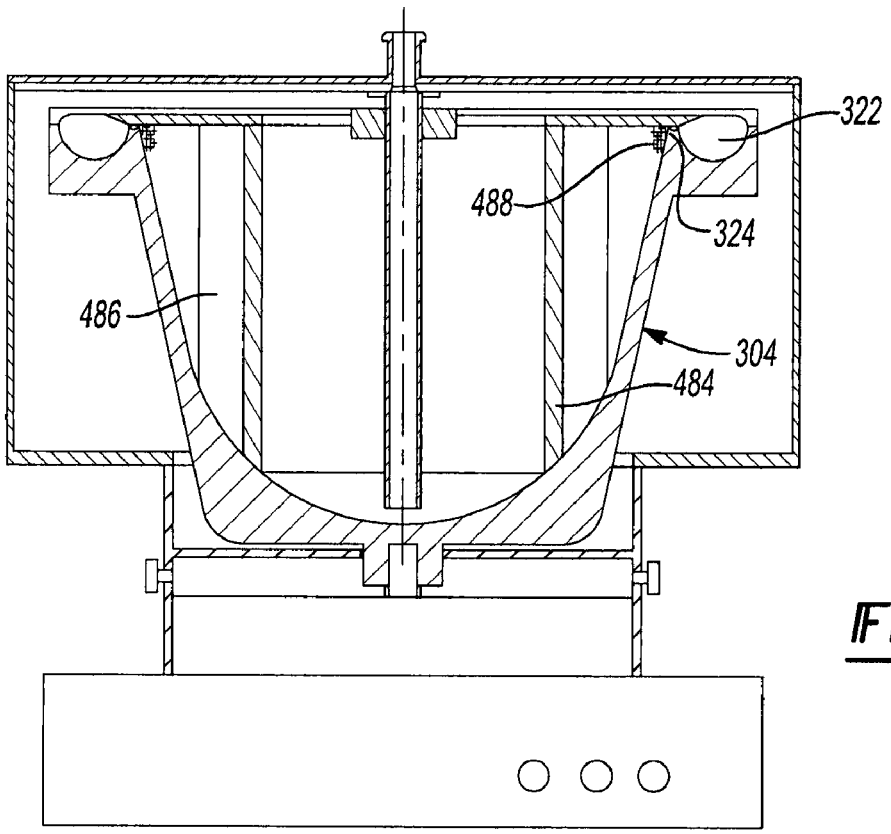

The rotation around the central axis 312 can initially cause the material to rise to a selected band within the inner chamber 304, as illustrated in FIG. 18C. The solution 480 can be moved to an appropriate location within the inner chamber 304 based upon the forces supplied with the rotation of the inner chamber 304 around the central axis 312. At a selected speed, a fat portion or oil portion 484 of the initial solution or sample can float near the central axis 312 on top of or closer to the central axis than an aqueous portion 486 of the initial sample, as illustrated in FIG. 18C. The initial separation of the fat portion 484 from the aqueous portion 486 can be achieved at a selected rotational speed or separation force. For example, the initial rotation can generate a force of about 10 to about 1000 times that of standard gravity on Earth (Gs). The rotation or centrifugation times can be any appropriate time. According to various embodiments, the rotation time can be about 60 seconds. A selected separation can occur, however, intraoperatively to allow for efficient autologous use of the selected cell fraction.

For example, a separation of the material positioned within the inner chamber 304 can be achieved through one or more spinning speeds or separation forces. Therefore, at an initial speed the fat portion 484 can be separated from the aqueous portion 486. The aqueous portion 486 can include various biological portions, such as cellular material, cellular matrix, and other appropriate materials. It will be further understood that the aqueous portion 486 can also include other materials, such as portions of whole blood, particularly if whole blood is introduced with the tissue sample in the initial solution 480.

At a selected time or after a selected period of time at a first separation force, a cellular material and/or cellular matrix (i.e. selected cell fraction) 488 can migrate to a top portion or near the seal portion 324 of the inner chamber 304. A second rotation speed or force can be about 300 Gs to about 3000 Gs. The migration of the cellular material 488 can be achieved after a selected period of rotation or at a selected rotational force. For example, a higher rotational speed or higher force can be applied to achieve a migration of the cellular material 488 towards the upper wall or the lid of the separation container 304 near the isolation annulus 322.

The separation of the selected cell fraction 488 from the remainder of the solution, including the aqueous portion 486 and the fat portion 484, can be achieved with a change in speed of rotation, a change in force, a time change in spinning of the material, or any appropriate separation. Nevertheless, once the cellular material, which can include pluripotent, multipotent, or stem cells, cellular matrix, growth factors, and other material, an isolation of the material can be achieved.

Figure 18E:
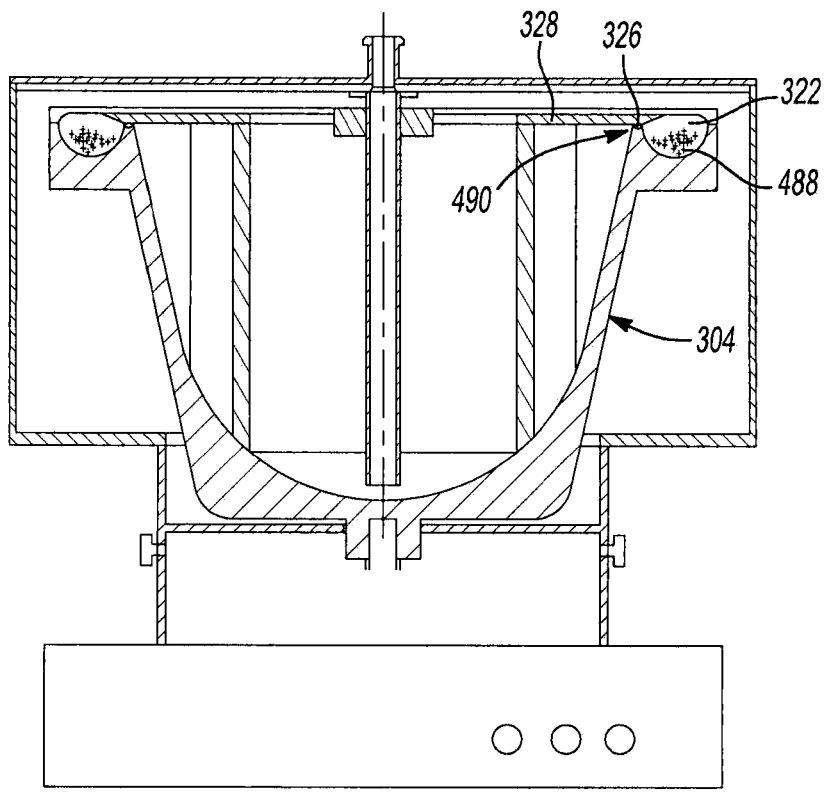
Figure 18F:
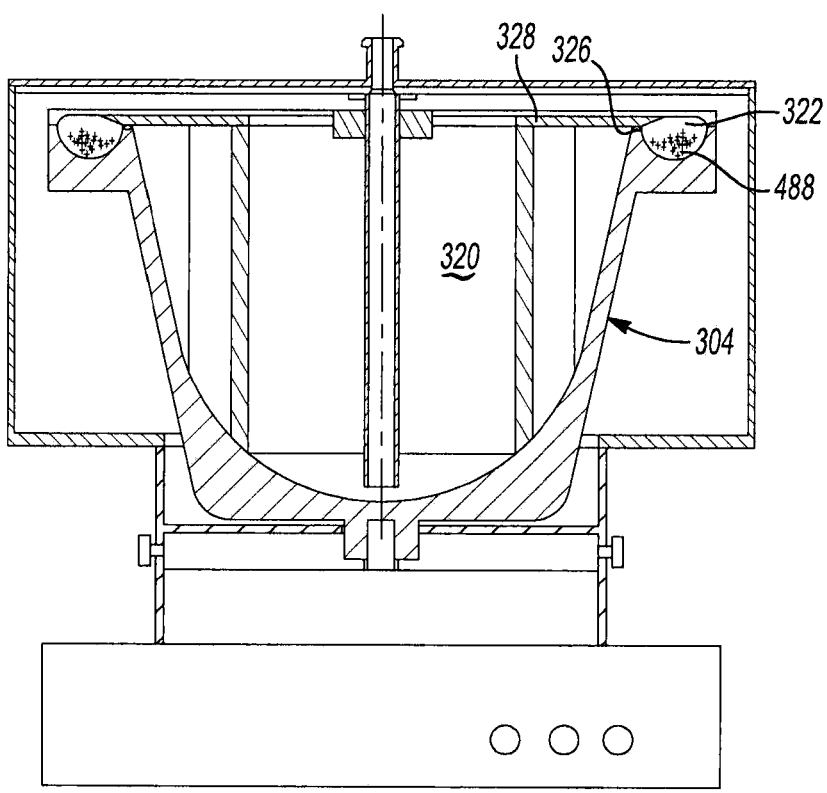

With reference to FIG. 18E, the lid 328 can move relative to the sealing member 326 to allow an opening 490 so that the cellular material 488 can be moved into the annular separation area 322. The lid 328 can move relative to the sealing member 326 for any appropriate reason. For example, electrical and/or mechanical systems can be used to open or move the lid relative to the sealing member 326. In addition, a selected force can be applied by the material within the separation chamber 320 to urge or force the lid to move or flex a selected amount opening a passage and allowing the cellular material 488 to move into the isolation area 322. For example, a third speed or force can be applied to the material within the separation chamber 304 such that it is forced against the lid 328 to move the lid relative to the sealing member 326 so that the cellular material 488 can move into the separation area 322. Therefore, the separation system 300 can allow for a substantially automatic isolation of the material based upon forces, such as centrifugal, created within the inner chamber 304, such as forces applied by the material positioned within the inner chamber 304 as created by spinning of the inner chamber 304 around the central axis 312.

If a speed is selected to achieve an opening or movement of the lid 328 relative to the sealing member 326, after a selected period of time, the speed of rotation can be changed to allow for the lid 328 to move back and engage the sealing member 326 to seal the lid onto the sealing member 326. The sealing of the lid 328 onto the sealing member 326 can substantially isolate the isolation area 322 from an area exterior to the isolation area 322, including the main separation area 320. Therefore, the isolation area 322 can be used to collect a selected material, such as cellular material, based upon a density or specific gravity of the cellular material 488 and a gravitational separation relative to the other material in the original solution 480.

Figure 18G:
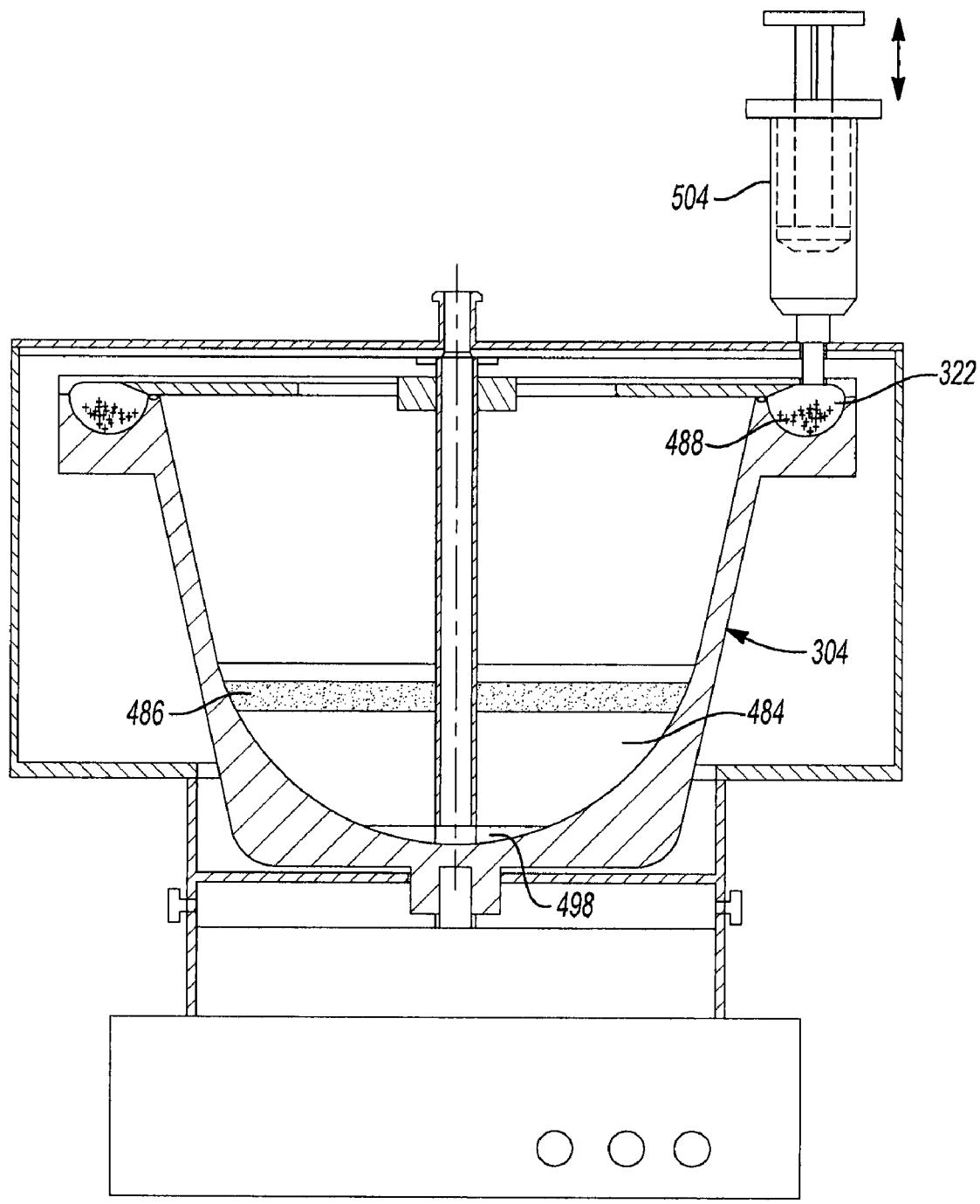

With reference to FIG. 18G, once the separation has completed, the spinning of the inner chamber 304 can be ceased for extraction of material from the inner chamber 304. The components can remain separated and may include the oil portion 484, the aqueous portion or purified fat 486, and excess or extraneous material 498. The cellular material 488, within the isolation chamber 322, can then be extracted via any appropriate extraction mechanism. For example, the selected cell fraction can be withdrawn via the extraction port or an extraction member that is positioned into the isolation area 322.

The isolation area 322 can include a barrier wall 344 to interrupt a complete annular ring of the isolation area 322. The barrier wall allows only a single path of extraction of material from the isolation area 322. The extraction port can be positioned near or at the wall 344 to allow for an efficient extraction of substantially all of the material positioned within the isolation area 322. Accordingly, a vacuum drawn at the wall 344 will urge substantially all of the material in the isolation area 322 out of the isolation area 322. It will be understood, as discussed above, that the optional vent 325, 325' can be provided to assist or allow extraction of the material from the isolation area 322.

The extraction or withdrawal of the selected cell fraction from the isolation area 322 can therefore, include various processes such as re-suspending the cellular material within a liquid material that is either positioned within the isolation area 322 from an external source or formed as a part of the separation. The re-suspension can be performed through reciprocation of an extraction syringe 500 that can form a jet of material within the isolation area 322. The formation of a jet can cause a re-suspension of the selected cell fraction 488 within the isolation area 322.

The various processes can achieve an enriched extraction of the selected cell population including stem cells, multipotent cells, or pluripotent cells from a tissue sample, such as adipose tissue. For example, the various processes, including the initial disruption to achieve a selected particle size, can allow for an efficient extraction of selected material from the tissue sample. The extraction can be efficient even without the use of extrinsic enzymes. Further, the isolation area 322 positioned relative to a main area 320 can allow for an efficient and rapid isolation of the cellular material 488 from the other material positioned within the interior chamber 304. In addition, the isolation area 322, substantially separated from other areas and forming a substantially non-continuous annular ring, can allow for re-suspension and efficient extraction of the cellular material. Therefore, the separation of the material can be both efficient and produce an extract that is highly enriched. The cell population extracted can be extracted in an appropriate and high yield from the tissue sample for various purposes. The application of the extracted cells can then be made to the patient from whom the tissue sample was acquired or to any other appropriate patient. The extracted cells can be provided for various purposes, such as healing, tissue regeneration, cell replacement therapy, scaffold seeding, cell line establishment or other uses.

According to various embodiments, the separation system and derived or separated selected cell fraction can be used to form an adipose-derived tissue implant containing pluripotent cells in a collagen extracellular matrix, comprising an extracellular matrix containing mechanically disrupted collagen substantially free of adipocytes and lipids and substantially or entirely free of extrinsic enzymes and comprised of greater than about 5% pluripotent cells. In addition, an adipose-derived tissue implant, as discussed above, can be derived where the tissue particle size is less than about 1 mm diameter. The implant may comprise blood components carried in the extracellular matrix, including growth factors and plasma, white blood cells, red blood cells, and platelets; as well as pluripotent cells carried in the extracellular matrix including fibroblasts, endothelial cells, smooth muscle cells, mast cells, pericytes, fibroblasts, lineage committed progenitor cells, and pre-adipocytes.

The pluripotent cells can be carried in the extracellular matrix, and the implant can be entirely or substantially free of extrinsic enzyme and the implant can be substantially free of adipocytes, and the isolated tissue of the pluripotent cell-containing extracellular matrix is comprised of single cells and clusters of up to about 0.10 cm in diameter. In addition, extracellular matrix may contain fragments of connective tissue, both free and associated with cells and cell clusters of diameters up to about 0.10 cm.

The adipose derived tissue implant containing pluripotent cells in a collagen extracellular matrix can be therapeutic for the various clinical indications, such as: fat transplantation for soft-tissue cosmesis, cartilage repair for either acute cartilage lesions or for osteoarthritic joints, skeletal muscle repair, cardiac muscle repair following a myocardial infarction, revascularization of critical limb ischemia, fracture repair, spine fusion, avascular necrosis, bone void fillers, augmentation of total joint arthroplasty, tendon reconstruction or repair, ligament reconstruction or repair, meniscus reconstruction or repair, wound healing or combinations thereof.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A method of separating a selected cell fraction from a sample volume, comprising:
    disrupting the sample volume to obtain a sample particle in a selected particle size range different than a sample volume particle size range prior to the disruption of the sample volume;
    separating the selected cell fraction from the sample particle, including,
        disposing the sample particle in a first section of a separation container;
        applying a first centrifugal force to the sample particle in the first section of the separation container;
        collecting the selected cell fraction in a second section of the separation container;
    removing the selected cell fraction from the second section of the separation container.

2. The method of claim 1, further comprising:
    spinning the separation container around a central axis to apply the centrifugal force to the sample particle;
    moving the sample particle along an interior wall of the first section of the separation container while spinning the separation container; and
    transferring the selected cell fraction into the second section of the separation container while spinning the separation container.

3. The method of claim 1, further comprising:
    mixing the at least one of the sample volume or the sample particle with citrate, a biologically acceptable acid, or EDTA prior to separating the selected cell fraction.

4. The method of claim 1, wherein disrupting the sample volume to obtain a sample particle in a selected particle size range includes forming the sample particle to have an average particle size in a range of about 0.1 mm to about 5 mm.

5. The method of claim 1, wherein disrupting the sample volume to obtain a sample particle in a selected particle size range includes forming the sample particle to have an average particle size in a range of about 0.5 mm to about 2 mm.

6. The method of claim 1, wherein disrupting the sample volume to obtain a sample particle in a selected particle size range includes forming the sample particle to have an average particle size of about 1 mm.

7. The method of claim 1 further comprising:
    disrupting the sample volume substantially only with a mechanical force applied to the sample volume to obtain the sample particle.

8. The method of claim 7, further comprising:
    obtaining the sample volume from a source body; and
    applying the selected cell fraction to the source body.

9. The method of claim 7, further comprising:
    obtaining the sample volume from a volume of adipose tissue of a patient;
    wherein disrupting the sample volume includes forming a plurality of sample particles.

10. The method of claim 1, further comprising:
    prior to applying a centrifugal force, forming a seal between the first section of the separation container and the second section; and
    removing the seal from between the first section of the separation container and the second section of the separation container upon application of an opening force due at least in part to the applied centrifugal force.

11. The method of claim 10, wherein applying the centrifugal force includes applying at least a first centrifugal force and a second opening centrifugal force, wherein the second opening centrifugal force includes the opening force;

wherein applying the second opening centrifugal force causes at least a portion of the selected cell fraction to exert a force on a lid that closes a passage between the first section to the second section to open the lid to allow the selected cell fraction to move from the first section to the second section allowing the collecting of the selected cell fraction.

12. The method of claim 10, further comprising:
flexing a portion of a lid to remove the seal from between the first section and the second section with the second opening centrifugal force.

13. The method of claim 10, further comprising:
moving a lid from a first lid position that is sealing the first section from the second section to a second lid position that is unsealing the first section from the second section.

14. The method of claim 1, further comprising:
collecting the selected cell fraction in a second section of the separation container includes moving the selected cell fraction to a sump; and
removing the selected cell fraction from the second section of the separation container includes applying a suction to the sump to remove the selected cell fraction.

15. A method of separating a selected cell fraction from a sample volume, comprising:
disrupting the sample volume to obtain a separable sample having a sample particle in a selected particle size range;
separating the selected cell fraction from the sample particle, including,
disposing the separable sample having the sample particle in a first section of a separation container having a first wall extending from a first bottom wall to an upper rim having an interior surface and an exterior surface;
applying a centrifugal force to the sample particle in the first section of the separation container to cause both (1) collecting the selected cell fraction in a collection section positioned near the upper rim and at least contacting the exterior surface of the first wall, the collection section having a second wall extending from a second bottom wall to the upper rim, and wherein the second bottom wall is nearer the upper rim than the first bottom wall and (2) moving a sealing section that seals a collection volume within the collection section when in a closed position to an open position by flexing a flexible section to allow the sealing section to move to the open position from the closed position; and
removing the selected cell fraction from the collection section of the separation container.

16. The method of claim 15, further comprising:
operating a drive motor to spin the separation container and the collection section simultaneously to apply the centrifugal force.

17. The method of claim 16, further comprising:
closing a housing to enclose all of the separation container, the collection section, the lid, the sealing section, the flexible section, and the drive motor.

18. The method of claim 15, further comprising:
placing a lid assembly extending over both the separation container and the collection section;
wherein in the closed position the sealing section selectively seals the collection volume from a container volume of the separation container;
wherein at a selected spin rate the applied centrifugal force the sealing section moves to the open position from the closed position;

applying a centrifugal force to the sample particle in the first section of the separation container to cause both (1) collecting the selected cell fraction in a collection section positioned near the upper rim and at least contacting the exterior surface of the first wall, the collection section having a second wall extending from a second bottom wall to the upper rim, and wherein the second bottom wall is nearer the upper rim than the first bottom wall and (2) moving a sealing section.

19. The method of claim 15, wherein disrupting the sample volume to obtain a separable sample having the sample particle in the selected particle size range includes forming the sample particle to have an average particle size in a range of about 0.1 mm to about 5 mm.

20. The method of claim 15, wherein disrupting the sample volume to obtain a separable sample having the sample particle in the selected particle size range includes forming the sample particle to have an average particle size in a range of about 0.5 mm to about 2 mm.

21. The method of claim 15, wherein disrupting the sample volume to obtain a separable sample having the sample particle in the selected particle size range includes moving the sample volume though a perforated member defining at least a through bore.

22. The method of claim 21, wherein moving the sample volume though a perforated member defining at least a through bore includes:
placing the sample volume in a sample containing volume having an end covered by the perforated member; and
moving a forcing member to force the sample volume through the perforated member to create the sample particle.

23. The method of claim 15, wherein removing the selected cell fraction from the collection section of the separation container includes:
drawing a vacuum within the collection section wherein a barrier wall defines a first end of the collection section on a first side of the barrier wall and a second end of the collection section on a second side of the barrier wall such that the barrier wall disrupts a complete annular well of the collection section;
wherein a vacuum is operable to be formed near the first end of the collection section to draw substantially all material out of the collection section through a port.

24. The method of claim 15, further comprising:
connecting a withdrawal device to a passage defined through a housing that encloses the separation container and the collection section.

25. A method of separating a selected cell fraction from a sample volume, comprising:
forming a separable volume having a sample particle in a selected particle size range from the sample volume;
disposing the formed sample particle in a first section of a separation container;
applying a first centrifugal force to the sample particle in the first section of the separation container while the first section is sealed relative to a second section of the separation container to cause at least a portion of the selected cell fraction to move within the first section of the separation container;
applying a second centrifugal force to the sample particle in the first section of the separation container to cause a sealing member to move from a sealed position to an unsealed position;
applying a third centrifugal force to the sample particle in the first section of the separation container after causing the sealing member to move to the unsealed position to allow at least the portion of the selected cell fraction to move into the second section of the separation container; and removing at least a portion of at least the portion of the selected cell fraction from the second section of the separation container.

26. The method of claim 25, wherein applying the centrifugal force includes spinning the separation container around a central axis which causes at least the selected cell fraction to move along an interior wall of the first section of the separation container and transfer at least the portion of the selected cell fraction into the second section of the separation container.

27. The method of claim 25, further comprising:
prior to applying the first centrifugal force, forming a seal between the first section of the separation container and the second section of the separation container with the sealing member.

28. The method of claim 27, wherein applying the first centrifugal force and applying the second centrifugal force are the same force at a first time and a second time, respectively.

29. The method of claim 28, wherein applying the second centrifugal force causes the seal member to move to the unsealed position.

30. The method of claim 29, wherein applying the second centrifugal force includes causing at least a portion of the selected cell fraction to exert a force on the sealing member to allow the selected cell fraction to move from the first section to the second section.

31. The method of claim 25, wherein applying at least the second centrifugal force includes flexing a portion of the sealing member to remove the seal from between the first section and the second section.

32. The method of claim 25, further comprising:
moving the selected cell fraction to a sump; and
applying a suction to the sump to remove the selected cell fraction.

33. The method of claim 25, further comprising:
moving the selected cell fraction to a sump by ceasing the application of the first centrifugal force, ceasing the application of the second centrifugal force, and ceasing the application of the third centrifugal force.

34. The method of claim 25, further comprising:
mixing the at least one of the sample volume or the sample particle with citrate, a biologically acceptable acid, or EDTA prior to at least one of forming a separable volume, disposing the formed sample particle in a first section of a separation container, applying a first centrifugal force, applying a second centrifugal force, or applying a third centrifugal force.

35. The method of claim 25, wherein forming the separable volume having the sample particle in the selected particle size range includes forming the sample particle to have an average particle size in a range of about 0.5 mm to about 2 mm.

36. The method of claim 25, wherein forming the separable volume having the sample particle in the selected particle size range includes disrupting the sample volume with only a mechanical force applied to the sample volume to obtain the sample particle.

37. The method of claim 36, wherein disrupting the sample volume with only a mechanical force includes moving the sample volume though a perforated member defining at least a through bore.

38. The method of claim 37, wherein moving the sample volume though a perforated member defining at least a through bore includes:
placing the sample volume in a sample containing volume having an end covered by the perforated member; and
moving a forcing member to force the sample volume through the perforated member to create the sample particle.

39. The method of claim 36, further comprising:
obtaining the sample volume from a source body; and
applying the selected cell fraction to the source body.

* * * * *